United States Patent [19]

Panzeri et al.

[11] Patent Number: 5,418,238
[45] Date of Patent: May 23, 1995

[54] 17β-SUBSTITUTED 4-AZA-5α-ANDROSTAN-3-ONE DERIVATIVES

[75] Inventors: Achille Panzeri, Merate; Marcella Nesi; Enrico di Salle, both of Milan, all of Italy

[73] Assignee: Farmitalia Carlo Erba S.R.L., Milan, Italy

[21] Appl. No.: 98,935

[22] Filed: Jul. 29, 1993

[30] Foreign Application Priority Data

Jul. 31, 1992 [GB] United Kingdom ............... 9216329

[51] Int. Cl.$^6$ ........................................... A61K 31/58
[52] U.S. Cl. ..................................... 514/284; 546/77; 544/125; 544/361
[58] Field of Search ................... 514/284; 546/77

[56] References Cited

U.S. PATENT DOCUMENTS 5,155,107 10/1992 Panzeri et al. .................. 546/77
5,302,621 4/1994 Kojima et al. .................. 514/284

FOREIGN PATENT DOCUMENTS 0155096 9/1985 European Pat. Off. .
0200859 11/1986 European Pat. Off. .
0271220 6/1988 European Pat. Off. .
0484094 5/1992 European Pat. Off. .

OTHER PUBLICATIONS

Liang et al. J. Steroid Biochem. vol. 19 No. 1 pp. 385–390 (1983).
Lamb et al. The Prostate vol. 21 pp. 15–34 (1992).
Stinson, Chem. and Eng. News, Jun. 29, 1992 pp. 7 and 8.
Journal of Medicinal Chemistry, vol. 29, No. 11, Nov. 1, 1986, Gary H. Rasmusson, et al., "Azasteroids: Structure–Activity Relationships for Inhibition of 5-α-Reductase and of Androgen Receptor Binding", pp. 2298–2315.
Journal of Medicinal Chemistry, vol. 27, No. 12, Dec. 1984, Gary H. Rasmusson, et al., "Azasteroids as Inhibitors of Rat Prostatic 5-α-Reductase", pp. 1690–1701.

Primary Examiner—Donald G. Daus
Attorney, Agent, or Firm—Oblon, Spivak, McClelland, Maier & Neustadt

[57] ABSTRACT

A compound of formula (I):

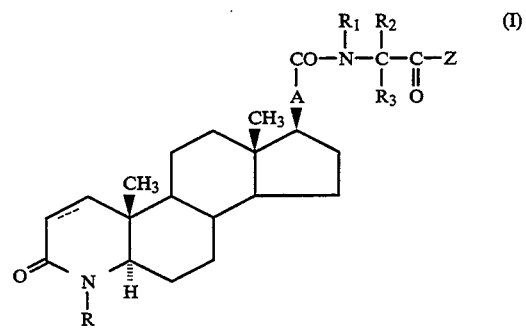

wherein
R is a hydrogen atom or a $C_1$–$C_4$ alkyl group;
A is a single bond or a straight or branched $C_1$–$C_6$ alkylene chain;
$R_1$ is a hydrogen atom or a $C_1$–$C_6$ alkyl group;
$R_2$ is a $C_1$–$C_6$ alkyl group, a $C_5$–$C_7$ cycloalkyl or a $C_6$–$C_{10}$ cycloalkylalkyl group, aryl or a $C_7$–$C_{10}$ arylalkyl group, or a $C_6$–$C_{10}$ heterocyclylalkyl group;
$R_3$ is hydrogen, a $C_1$–$C_4$ alkyl group or an aryl or a $C_7$–$C_{10}$ arylalkyl group;
Z is a $C_1$–$C_6$ alkyl group, an —$OR_5$ group wherein $R_5$ is a $C_1$–$C_6$ alkyl group,

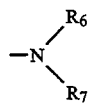

group wherein each of $R_6$ and $R_7$ is hydrogen, $C_1$–$C_6$ alkyl, $C_5$–$C_7$ cycloalkyl, phenyl or $R_6$ and $R_7$ taken together with the nitrogen to which they are linked form a pentatomic or hexatomic saturated heteromonocyclic ring; and the symbol ---- represents a single or a double bond, is a testosterone 6β 5α-reductase inhibitor and is therapeutically useful in benign prostatic hyperplasia, prostatic and breast cancers, seborrhoea, female hirsutism and male pattern baldness.

4 Claims, No Drawings

17β-SUBSTITUTED 4-AZA-5α-ANDROSTAN-3-ONE DERIVATIVES

The present invention relates to novel 17β-substituted 4-aza-5α-androstan-3-one derivatives, to a process for their preparation, and to pharmaceutical compositions containing them. These compounds are inhibitors of androgen action, by means of testosterone 5α-reductase inhibition.

In certain androgen responsive tissues the action of testosterone is mediated primarily through its 5α-reduced metabolite, dihydrotestosterone (DHT) (Bruchowsky N., Wilson J. D.; J. Biol. Chem. 243, 5953, 1968). The conversion of testosterone to dihydrotestosterone is catalysed by the enzyme 5α-reductase and if 5α-reductase is inhibited, the formation of dihydrotestosterone is reduced and its specific androgenic effect is attenuated or prevented.

The 5α-reductase inhibitors may find medical application for the treatment of hyperandrogenic conditions, e.g. certain prostatic diseases, such as benign prostatic hyperplasia and prostatic cancer, and certain skin-hair conditions, such as ache, seborrhoea, female hirsutism and male pattern baldness (Siiteri P. K., Wilson J. D., J. Clin. Invest. 49, 1737, 1970; Price V. H., Arch. Dermatol. III, 1496, 1975; Sandberg A. A., Urology, 17, 34, 1981). Also breast cancer treatment can take advantage from use of 5α-reductase inhibitors as the said tumour is known to be aggravated by presence of androgens. Androst-4-en-3-one-17β-carboxylic acid and its methyl ester (Voigt and Hsia, Endocrinology, 92, 1216 (1973); Canadian Patent No. 970,692) are among the first steroidic compounds described as 5α-reductase inhibitors.

Two 5,10-secosteroids having a 3-keto-4,5-diene system in the expanded ring have been found to be selective inhibitors of rat epididymal 5α-reductase (Robaire et al., J. Steroid Biochem. 8, 307–310 (1977)).

The (20R)-4-diazo-21-hydroxy-20-methyl-5α-pregnan-3-one and its analogs are reported to be enzyme activated inhibitors of testosterone 5α-reductase (Blohm et al., Biochem. Biophys. Res. Comm. 95, 273–80 (1980); U.S. Pat. No. 4,317,817).

Another series of enzyme-directed irreversible inhibitors of 5α-reductase have been prepared by introducing a 6-methylene moiety into substrates type 3-keto-$\Delta^4$-progestins and androgens (Petrow et al., Steroids 38, 352–53 (1981); U.S. Pat. No. 4,396,615)).

More recently unsaturated derivatives of 3-carboxy steroids have been reported as uncompetitive 5α-reductase inhibitors versus testosterone (Biorg. Chem. 17, 372–376 (1989); Eur. Pat. Appln. no. 0289327).

4-Aza steroids are by far the most studied steroid 5α-reductase inhibitors. The compounds known in the art are reported in a very large number of publications and patents. In particular the 17β-acylamides and their metabolites are described in: J. Med. Chem. 27, 1690–1701 (1984), J. Med. Chem. 29, 2298–2315 (1986), Eur. Pat. Appln. No. 0004949; U.S. Pat. No. 4,377,584; Eur. Pat. Appln. 0155096; U.S. Pat. No. 4,845,104; Eur. Pat. Appln. 0462662; Eur. Pat. Appln. 0484094 A2; U.S. Pat. No. 4,859,681; WO 91/12261.

The invention provides compounds of the following formula (I)

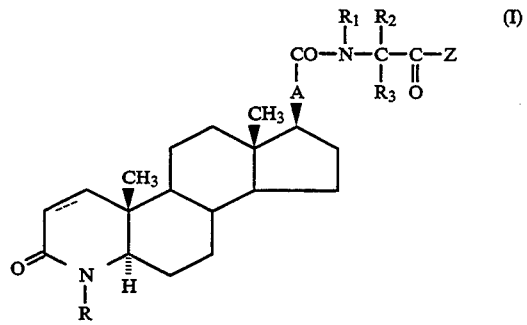

wherein

R is a hydrogen atom or a $C_1$–$C_4$ alkyl group unsubstituted or substituted by one or more fluorine atoms;

A is a single bond or a straight or branched $C_1$–$C_6$ alkylene chain;

$R_1$ is a hydrogen atom or a $C_1$–$C_6$ alkyl group unsubstituted or substituted by one or more fluorine atoms;

$R_2$ is:
a) a $C_1$–$C_6$ alkyl group unsubstituted or substituted by one or more substituents chosen from fluoro, $C_1$–$C_4$ alkoxycarbonyl, carbamoyl, carboxy, hydroxy, $C_1$–$C_4$ alkoxy, amino, di-$C_1$–$C_4$ alkylamino, mercapto and $C_1$–$C_4$ alkylthio, or b) a $C_3$–$C_7$ cycloalkyl or a $C_6$–$C_{10}$ cycloalkylalkyl group, unsubstituted or substituted by one or more fluorine atoms, or c) an aryl or a $C_7$–$C_{10}$ arylalkyl group, unsubstituted or ring substituted by one or more substituents chosen from halogen, $C_1$–$C_4$ alkyl, $C_1$–$C_4$ alkoxy, hydroxy and trifluoromethyl, or d) a $C_6$–$C_{10}$ heterocycloalkyl group in which the heterocyclic ring contains one or more heteroatoms chosen from N, C and S, unsubstituted or ring substituted by one or more fluorine atoms;

$R_3$ is hydrogen, a $C_1$–$C_4$ alkyl group or an aryl or a $C_7$–$C_{10}$ arylalkyl group, unsubstituted or ring substituted by one or more substituents chosen from halogen, $C_1$–$C_4$ alkyl, $C_1$–$C_4$ alkoxy, hydroxy and trifluoromethyl;

Z is:
a') a $C_1$–$C_6$ alkyl group unsubstituted or substituted by one or more fluorine atoms, b') an —$OR_5$ group wherein $R_5$ is a $C_1$–$C_6$ alkyl group, c') a

group wherein each of $R_6$ and $R_7$, independently, is hydrogen, $C_1$–$C_6$ alkyl, $C_5$–$C_7$ cycloalkyl or phenyl or $R_6$ and $R_7$ taken together with the nitrogen to which they are linked form a pentatomic or hexatomic saturated heteromonocyclic ring, optionally containing at least one additional heteroatom selected from oxygen and nitrogen; and the symbol ⎓ represents a single or a double bond; provided that when Z is a group $OR_5$, $R_2$ is not an unsubstituted $C_1$–$C_6$ alkyl group; and the pharmaceutically acceptable salts thereof.

In the formulae of this specification the dotted line ("""") indicates a substituent in the α-configuration, i.e. below the plane of the ring, and the wedged line (▲) indicates a substituent in the β-configuration, i.e. above the plane of the ring. The configurations of the chiral centers in the side chain is unspecified; the invention is meant to include both the single "R" and "S" epimers as well as their "R,S" mixtures.

The invention includes the pharmaceutically acceptable salts of the compounds of formula (I) which contain a salifiable group.

It is known in the chemical literature that α-fluorinated ketones form stable gem-diols with water; so they are sometimes obtained as a mixture of a hydrate form and a ketone form, whose ratio depends on steric and electronic factors (Hudlicky H., Chemistry of Organic fluorine compounds, 2nd edition, Ellis Horwood Ltd.)

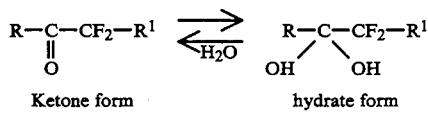

Ketone form      hydrate form

In this specification the α-fluorinated ketones are meant to include both these forms, i.e. they may exist in the pure ketone form or in the pure hydrate (gem-diol) form or as a mixture of both ketone and hydrate form.

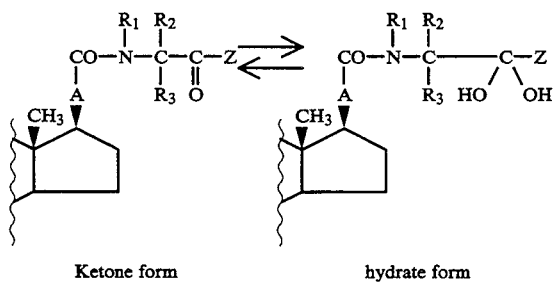

Ketone form      hydrate form

The invention includes also all the possible isomers of formula (I) and their mixtures.

Also the metabolites and the metabolic precursors of the compounds of formula (I) are within the scope of the present invention.

In this specification the alkyl groups and the aliphatic portions of the arylalkyl, cycloalkylalkyl and the heterocyclic alkyl groups may be straight or branched chain.

A $C_1$-$C_4$ alkyl group may be, for example, methyl, ethyl, isopropyl, n-butyl or tert-butyl. The $C_1$-$C_4$ alkyl group may be unsubstituted or substituted by one or more preferably one, two or three, fluorine atoms and in particular may be difluoromethyl, fluoromethyl, trifluoromethyl or 2,2,2-trifluoroethyl.

A $C_1$-$C_6$ straight or branched alkylene chain may be, for example, a straight or branched $C_1$-$C_4$ alkylene chain, in particular,

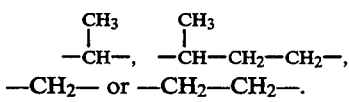

—$CH_2$— or —$CH_2$—$CH_2$—.

A $C_1$-$C_6$ alkyl group may be, for example, methyl, ethyl, n-propyl, isopropyl, n-butyl, isobutyl, sec-butyl, tert-butyl, n-pentyl, iso-pentyl, neopentyl, n-hexyl or isohexyl. The $C_1$-$C_6$ alkyl group may be unsubstituted or substituted by one or more, preferably 1, 2, 3, 4, 5 or 6, fluorine atoms and may be, in particular, fluoromethyl, difluromethyl, trifluoromethyl, 2,2,2-trifluoroethyl, 3,3,3-trifluoropropyl, 4,4,4-trifluorobutyl, 1-trifluoromethylethyl, 2-trifluoromethylprop-1-yl, pentafluoroethyl, 1,1,1,3,3,3-hexafluoroprop-2-yl or 4,4,5,5,5-pentafluoropentyl.

A $C_1$-$C_4$ alkoxycarbonyl group may be, for example, methoxy-, ethoxy-, propoxy- or butoxycarbonyl, preferably methoxycarbonyl.

A $C_1$-$C_4$ alkoxy group may be, for example, methoxy, ethoxy, propoxy or butoxy, preferably methoxy.

A di-($C_1$-$C_4$-alkyl) amino may be, for example, dimethylamino. A $C_1$-$C_4$ alkylthio group may be, for example, methylthio, ethylthio, propylthio, or butylthio, preferably methylthio or ethylthio.

A $C_1$-$C_6$ alkyl group wherein one or more hydrogen atoms are substituted by one or more substituents other than fluorine may be, for example $CH_2SH$, $CH_2SCH_2CH_3$, $CH_2CH_2SCH_3$, $CH_2OH$, $CH_2OCH_3$, $CH(OH)CH_3$, $CH(OCH_3)CH_3$, $CH_2CONH_2$, $CH_2CH_2CONH_2$, $CH_2COOH$, $CH_2CH_2COOH$, $CH_2CH_2CH_2CH_2NH_2$,

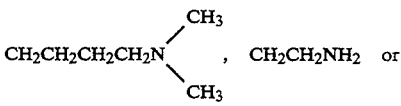, $CH_2CH_2NH_2$ or

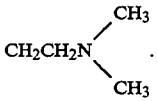.

A $C_5$-$C_7$ cycloalkyl may be, for example, cyclopentyl, cyclohexyl or cycloheptyl.

A $C_6$-$C_{10}$ cycloalkylalkyl group may be, for example, a ($C_5$-$C_7$ cycloalkyl) alkyl, preferably ($C_5$-$C_7$ cycloalkyl) methyl or ($C_5$-$C_7$ cycloalkyl) ethyl, in particular, cyclohexylmethyl, cyclohexylethyl, cyclopentylmethyl unsubstituted or substituted by one or more, preferably one, fluorine atoms, in particular, 1-fluoro-1-cyclohexylmethyl.

An aryl group may be, for example, phenyl unsubstituted or substituted by one or more, preferably one, chloro, bromo, fluoro, $C_1$-$C_4$ alkyl, preferably methyl, $C_1$-$C_4$ alkoxy, preferably methoxy, hydroxy, or trifluoromethyl groups, in particular, 4-methylphenyl, 4-hydroxyphenyl, 4-methoxyphenyl, 4-trifluoromethylphenyl, 4-fluorophenyl.

A $C_7$-$C_{10}$ arylalkyl group may be, for example, phenyl ($C_1$-$C_4$ alkyl), preferably benzyl, unsubstituted or ring substituted by one or more, preferably one or two, chloro, bromo, fluoro, $C_1$-$C_4$ alkoxy preferably methoxy, hydroxy or trifluoromethyl groups, in particular 4-hydroxybenzyl, 4-methoxybenzyl, 4-hydroxy-3-methoxybenzyl, 3,4-dimethoxybenzyl, 4-trifluoromethylbenzyl, 2-fluorobenzyl, 3-fluorobenzyl, 4-fluorobenzyl, 3-fluoro-4-hydroxybenzyl.

A $C_6$-$C_{10}$ heterocyclolalkyl group may be, for example, heterocyclo ($C_1$-$C_4$ alkyl), for example heterocyclomethyl, preferably imidazolyl-methyl or indolyl-methyl, unsubstituted or ring substituted by one or more, preferably one, fluorine atoms, in particular, (4-imidazolyl)-methyl, (3-indolyl)-methyl, (5-fluoroindolyl)methyl, (6-fluoroindolyl)methyl or (3-imidazolyl)methyl.

In the above formula (I) R is, preferably, hydrogen, methyl, ethyl, fluoromethyl, or 2,2,2-trifluoroethyl.

A is, preferably, a bond or

$R_1$ is, preferably, hydrogen or methyl.

$R_2$ is, preferably, the side-chain of the most common natural and unnatural amino acids, unsubstituted or substituted by one or more fluorine atoms.

When $R_2$ is an unsubstituted $C_1$–$C_6$ alkyl group, it is preferably methyl, ethyl, n-propyl, iso-propyl, n-butyl, iso-butyl, sec-butyl, tert-butyl, n-pentyl, iso-pentyl, n-hexyl or iso-hexyl.

When $R_2$ is a substituted $C_1$–$C_6$ alkyl group, it is preferably —$CH_2F$, —$CHF_2$, —$CF_3$, $CF_3$—$CH_2$—, $CF_3$—$CH_2$—$CH_2$—, $CF_3$—$CH_2$—$CH_2$—$CH_2$—, $CH_3$—$\overset{CF_3}{\underset{|}{CH}}$—, $CH_3$—$\overset{CF_3}{\underset{|}{CH}}$—$CH_2$, $CF_3$—$\overset{CF_3}{\underset{|}{CH}}$—, $CF_3$—$CF_2$—$CH_2$—$CH_2$—$CH_2$—, $CH_3O$—$CH_2$— or $CH_3$—S—$CH_2$—$CH_2$—. When $R_2$ is $C_5$–$C_7$ cycloalkyl, it is preferably cyclohexyl. When $R_2$ is $C_6$–$C_{10}$ cycloalkylalkyl, it is preferably cyclohexylmethyl. When $R_2$ is aryl, it is preferably phenyl or benzyl. When $R_2$ is $C_7$–$C_{10}$ arylalkyl, it is preferably benzyl. When $R_2$ is heterocycloalkyl, it is preferably (3-imidazolyl)methyl or (3-indolyl)methyl. $R_3$ is preferably hydrogen, methyl, ethyl, phenyl or benzyl. When Z is $C_1$–$C_6$ alkyl as defined above under a'), it is preferably methyl, ethyl, trifluoromethyl, 2,2,2-trifluoroethyl, pentafluoroethyl, n-propyl, n-butyl or sec-butyl. When Z is a group $OR_5$ as defined above under b'), $R_5$ is preferably methyl, ethyl or t-butyl. When Z is a group

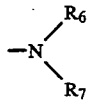

as defined above under c') it is preferably —$NH_2$, —$NHCH_3$, —$NHC_2H_5$, —$NHCH(CH_3)_2$, —$NHC(CH_3)_3$, —$NHCH_2C(CH_3)_3$, —$N(C_2H_5)_2$, —$N[CH(CH_3)_2]_2$,

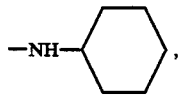

NH-Ph, piperidyl, piperazinyl or morpholino.

Pharmaceutically acceptable salts of the compounds of the invention include acid addition salts with inorganic, e.g. nitric, hydrochloric, hydrobromic, sulphuric, perchloric and phosphoric, acids or organic, e.g. acetic, propionic, glycolic, lactic, oxalic, malonic, malic, maleic, tartaric, citric, benzoic, cinnamic, mandelic and salicylic, acids, and salts with pharmaceutically acceptable bases, either inorganic bases, such as, for example, alkali metal, e.g., sodium or potassium, or alkaline-earth metal, e.g., calcium or magnesium, or zinc or aluminium hydroxides, or organic bases such as, for instance, aliphatic amines as, e.g., methylamine, diethylamine, tri-methylamine, ethylamine and heterocyclic amines, e.g., piperidine.

Preferred compounds of formula (I) are those wherein:

R is hydrogen or methyl;
A is a single bond;
$R_1$ is hydrogen;
$R_2$ is methyl, iso-propyl or iso-butyl, sec-butyl, tert-butyl, trifluoromethyl, 1-trifluoromethyleth-1-yl, 2-trifluoromethylprop-1-yl, 2-methylthioeth-1-yl methoxymethyl, phenyl or benzyl;
$R_3$ is hydrogen or methyl;
Z is methyl, n-butyl, trifluoromethyl, pentafluoroethyl, a group $OR_5$ wherein $R_5$ is methyl, ethyl or tert-butyl; or a group

wherein each of $R_6$ and $R_7$ is, independently, hydrogen, ethyl, isopropyl or neopentyl; and the symbol $\text{---}$ represents a single or a double bond provided that, when Z is a group $OR_5$ as-defined hereinabove, $R_2$ is trifluoromethyl, 1-trifluoromethyleth-1-yl, 2-trifluoromethylprop-1-yl, 2-methylthioethyl, methoxymethyl, phenyl or benzyl.

Examples of specific compounds preferred under this invention are:

1) N-(1-neopentylcarbamoyleth-1-yl) 3-oxo-4-aza-5α-androstane-17β-carboxamide;
2) N-(1-neopentylcarbamoyleth-1-yl) 3-oxo-4-aza-5α-androst-1-ene-17β-carboxamide;
3) N-[3-oxobut-2-yl]3-oxo-4-aza-5α-androstane-17β-carboxamide;
4) N-[3-oxohept-2-yl]3-oxo-4-aza-5α-androst-1-ene-17β-carboxamide;
5) N-[1,1,1-trifluoro-2-oxobut-3-yl]3-oxo-4-aza-5α-androst-1-ene-17β-carboxamide;
6) N-[4-methyl-2-oxopent-3-yl]3-oxo-4-aza-5α-androst-1-ene-17β-carboxamide;
7) N-[1,1,1-trifluoro-4-methyl-2-oxopent-3-yl]3-oxo-4-aza-5α-androst-1-ene-17β-carboxamide;
8) N-[5-methyl-2-oxohex-3-yl]3-oxo-4-aza-5α-androst-1-ene-17β-carboxamide;
9) N-[4-methyl-2-oxohex-3-yl]3-oxo-4-aza-5α-androst-1-ene-17β-carboxamide;
10) N-[4,4-dimethyl-2-oxopent-3-yl]3-oxo-4-aza-5α-androst-1-ene-17β-carboxamide;
11) N-[1,1,1-trifluoro-3-oxobut-2-yl]3-oxo-4-aza-5α-androst-1-ene-17β-carboxamide;
12) N-[2,2,2-trifluoro-1-methoxycarbonyleth-1-yl]3-oxo-4-aza-5α-androst-1-ene-17β-carboxamide;
13) N-[5,5,5-trifluoro-4-methyl-2-oxopent-3-yl]3-oxo-4-aza-5α-androst-1-ene-17β-carboxamide;
14) N-[3,3,3-trifluoro-2-methyl-1-methoxycarbonyl-prop-1-yl]3-oxo-4-aza-5α-androst-1-ene-17β-carboxamide;
15) N-[6,6,6-trifluoro-5-methyl-2-oxohex-3-yl]3-oxo-4-aza-5α-androst-1-ene-17β-carboxamide;
16) N-[4,4,4-trifluoro-3-methyl-1-methoxycarbonyl-but-1-yl]3-oxo-4-aza-5α-androst-1-ene-17β-carboxamide;
17) N-[5-methylthio-2-oxopent-3-yl]3-oxo-4-aza-5α-androst-1-ene-17β-carboxamide;

18) N-[3-methylthio-1-methoxycarbonylprop-1-yl]3-oxo-4-aza-5α-androst-1-ene-17β-carboxamide;
19) N-[4-methoxy-2-oxobut-3-yl]3-oxo-4-aza-5α-androst-1-ene-17β-carboxamide;
20) N-[2-methoxy-1-methoxycarbonyleth-1-yl]3-oxo-4-aza-5α-androst-1-ene-17β-carboxamide;
21) N-[3-oxobut-2-yl]3-oxo-4-aza-5α-androst-1-ene-17β-carboxamide;
22) N-[1,1,1-trifluoro-3-methyl-2-oxobut-3-yl]3-oxo-4-aza-5α-androst-1-ene-17β-carboxamide;
23) N-[3-methyl-2-oxobut-3-yl]3-oxo-4-aza-5α-androst-1-ene-17β-carboxamide;
24) N-[1,1,1-trifluoro-2-oxo-4-phenylbut-3-yl]3-oxo-4-aza-5α-androst-1-ene-17β-carboxamide;
25) N-[1,1,1-trifluoro-2-oxo-3-phenylpropyl) 3-oxo-4-aza-5α-androst-1-ene-17β-carboxamide;
26) N-[1,1,1-trifluoro-3-methyl-2-oxo-3-phenylpropyl]3-oxo-4-aza-5α-androst-1-ene-17β-carboxamide;
27) N-[1,1,1,2,2-pentafluoro-3-oxopent-4-yl]3-oxo-4-aza-5α-androst-1-ene-17β-carboxamide.

compounds, according to their number, are tabulated below, with reference to the substituents as defined for formula (I):

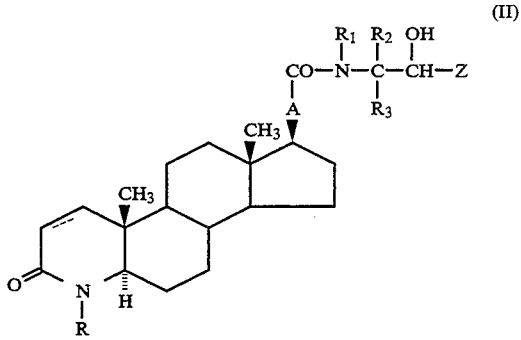

wherein R, $R_1$, $R_2$, $R_3$, A and the symbol ⚌ are as defined above and Z is a $C_1$–$C_6$ alkyl group, unsubstituted or substituted by one of more fluorine atoms, so obtaining a compound of formula (I) wherein R, $R_1$, $R_2$, $R_3$, A and the symbol ⚌ are as defined above and Z is a $C_1$–$C_6$ alkyl group unsubstituted or substituted by one or more fluorine atoms; or (2) reacting a compound of formula (III)

| | R | A | $R_1$ | $R_2$ | $R_3$ | Z | ⚌ |
|---|---|---|---|---|---|---|---|
| 1) | H | bond | H | $CH_3$ | H | NH(neopentyl) | single |
| 2) | H | bond | H | $CH_3$ | H | NH(neopentyl) | double |
| 3) | H | bond | H | $CH_3$ | H | $CH_3$ | single |
| 4) | H | bond | H | $CH_3$ | H | n-butyl | double |
| 5) | H | bond | H | $CH_3$ | H | $CF_3$ | double |
| 6) | H | bond | H | iso-propyl | H | $CH_3$ | double |
| 7) | H | bond | H | iso-propyl | H | $CF_3$ | double |
| 8) | H | bond | H | iso-butyl | H | $CH_3$ | double |
| 9) | H | bond | H | sec-butyl | H | $CH_3$ | double |
| 10) | H | bond | H | tert-butyl | H | $CH_3$ | double |
| 11) | H | bond | H | $CF_3$ | H | $CH_3$ | double |
| 12) | H | bond | H | $CF_3$ | H | $OCH_3$ | double |
| 13) | H | bond | H | $CH_3$–CH(–$CF_3$)– | H | $CH_3$ | double |
| 14) | H | bond | H | $CH_3$–CH(–$CF_3$)– | H | $OCH_3$ | double |
| 15) | H | bond | H | ($CF_3$)($CH_3$)CH–$CH_2$– | H | $CH_3$ | double |
| 16) | H | bond | H | ($CF_3$)($CH_3$)CH–$CH_2$– | H | $OCH_3$ | double |
| 17) | H | bond | H | $CH_3$–S–$CH_2$–$CH_2$– | H | $CH_3$ | double |
| 18) | H | bond | H | $CH_3SCH_2$–$CH_2$ | H | O–$CH_3$ | double |
| 19) | H | bond | H | $CH_3$–O–$CH_2$ | H | $CH_3$ | double |
| 20) | H | bond | H | $CH_3$–O–$CH_2$ | H | O–$CH_3$ | double |
| 21) | H | bond | H | $CH_3$ | H | $CH_3$ | double |
| 22) | H | bond | H | $CH_3$ | $CH_3$ | $CF_3$ | double |
| 23) | H | bond | H | $CH_3$ | $CH_3$ | $CH_3$ | double |
| 24) | H | bond | H | $PhCH_2$ | H | $CF_3$ | double |
| 25) | H | bond | H | Ph | H | $CF_3$ | double |
| 26) | H | bond | H | Ph | $CH_3$ | $CF_3$ | double |
| 27) | H | bond | H | $CH_3$ | H | $CF_2CF_3$ | double |

The compounds of formula (I) may be obtained by a process comprising:
(1) oxidizing a compound of formula (II)

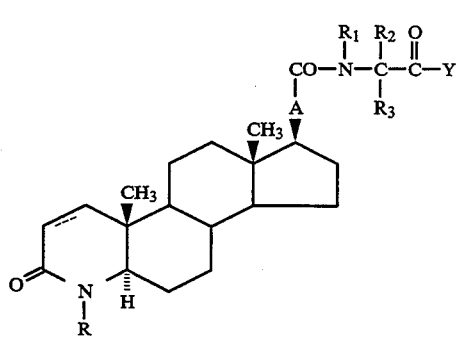
(III)

wherein R, $R_1$, $R_2$, $R_3$, A and the symbol ---- are as defined above and Y is OH or an activating group of the carboxy function with a compound of formula (IV)

(IV)

wherein $R_6$ and $R_7$ are as defined above so obtaining a compound of formula (I) wherein R, $R_1$, $R_2$, $R_3$, A and the symbol ---- are as defined above and Z is a

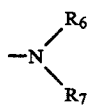

group as defined above; or (3) reacting a compound of formula (III) as defined above with a compound of formula (V)

$R_6$—M      (V)

wherein $R_6$ is a $C_1$–$C_6$ alkyl group unsubstituted or substituted by one or more fluorine atoms and M is a metal atom or a metal-halogen group so obtaining a compound of formula (I) wherein R, $R_1$, $R_2$, $R_3$, A and the symbol ---- are as defined above and Z is a $C_1$–$C_6$ alkyl group unsubstituted or substituted by one or more fluorine atoms; or (4) reacting a compound of formula (VI)

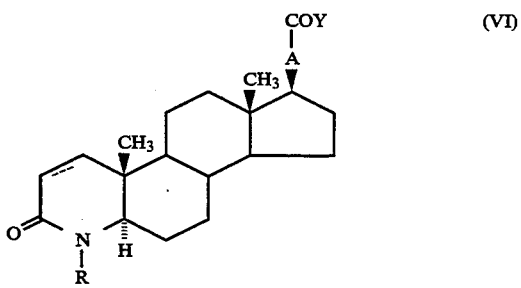
(VI)

wherein R, A and ---- are as defined above and Y is OH or an activating group of the carbon function with a compound of formula (VII)

(VII)

wherein $R_1$, $R_2$, $R_3$ and Z are as defined above, so obtaining a compound of formula (I) wherein R, $R_1$, $R_2$, $R_3$, A, Z and the symbol ---- are as defined above; and if desired, (5) dehydrogenating a compound of formula (I) wherein R, $R_1$, $R_2$, $R_3$, A and Z are as defined above and the symbol ---- is a single bond, so obtaining a corresponding compound of formula (I) wherein R, $R_1$, $R_2$, $R_3$, A and Z are as defined above and the symbol ---- is a double bond, and, if desired, converting a compound of formula (I) into a pharmaceutically acceptable salt thereof and/or if desired separating a mixture of isomers of formula (I) into the single isomers.

The oxidation of a compound of formula (II), according to the process variant (1), may be carried out according to the Swern methodology, as described in Synthesis 1981, 165.

In particular, the oxidation may be carried out treating the compound dissolved in a solvent such as, for example, methylene chloride with dimethylsulphoxide and oxalyl chloride, at a temperature ranging from about −78° C. to room temperature for a time varying from about 15 minutes to about 2 hours.

When Y is an activating group in the compound of formula (III) and (VI), it may be any suitable activating group of the carboxy function which is useful in the formation of amidic or peptidic linkages. It may be, for instance, one of the following groups:

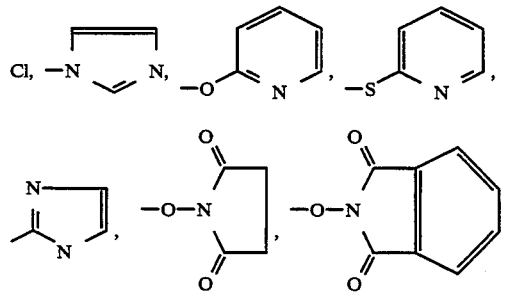

The reaction of a compound of formula (III) with a compound of formula (IV), according to the process variant (2), may be carried out in an inert solvent such as, for example, $CH_2Cl_2$, THF, AcOEt, DMF, benzene or toluene, at a temperature ranging from about 0° C. to about 100° C., optionally in the presence of an organic base such as, for example, pyridine, p-dimethylaminopyridine or triethylamine for a time varying from about one hour to about 24 hours.

In the compounds of formula (V) when M is a metal atom it is preferably Li and when it is a metal-halogen group is preferably MgCl, MgBr or MgI.

The reaction between a compound of formula (III) and a compound of formula (V), according to process variant (3), may be carried out in an anhydrous solvent such as THF, $Et_2O$, dioxane, benzene under argon or nitrogen atmosphere at a temperature ranging from about −100° C. to about the refluxing temperature of the solvent, for a time varying from about half an hour to about 24 hours.

A reaction between a compound of formula (VI) and a compound of formula (VII), according to the process variant (4), may be carried out, e.g., in an inert solvent such as, for example, $CH_2Cl_2$, THF, AcOEt, DMF or benzene, at a temperature ranging from about 0° C. to about 100° C., optionally in the presence of an organic base such as, for example, pyridine, p-dimethylaminopyridine or triethylamine, for a time varying from about one hour to about 5 days.

The compounds of formula (VII) are often used as N-salt-derivatives, preferably hydrochlorides, hydrobromides or trifluoroacetates, and the free amino group is formed in situ in the presence of an organic base such as, for example, pyridine, or a tri-$C_1$-$C_6$-alkylamine, preferably triethylamine.

The dehydrogenation of a compound of formula (I) according to the process variant (5), may be carried out with a dehydrogenating agent, e.g., benzeneseleninic anhydride or DDQ, in an anhydrous solvent such as, for example, chlorobenzene, dioxane, xylene, toluene, benzene, optionally in the presence of bis(trimethylsilyl)trifluoroacetamide (BSTFA) (especially when DDQ is used), at a temperature ranging from room temperature to the reflux temperature of the solvent, for a time varying from about two hours to 24 hours, preferably in an inert atmosphere of nitrogen.

Standard procedures may be used for separating a mixture of isomers of formula (I) into single isomers.

The present invention also provides compounds of formula (II) wherein R, $R_1$, $R_2$, $R_3$, A and the symbol ⁓ have all the same meanings as for the compounds of formula (I) and Z is a $C_1$-$C_6$ alkyl group unsubstituted or substituted by one or more fluorine atoms, with the proviso that at least one of the groups, R, $R_1$, $R_2$, $R_3$ and Z contains at least one fluorine atom, and the pharmaceutically acceptable salts thereof.

A preferred class of compounds of formula (II) according to the invention are the compounds of formula (II) wherein:
 R is hydrogen or methyl;
 A is a single bond;
 $R_1$ is hydrogen;
 $R_2$ is methyl, iso-propyl, iso-butyl, sec-butyl, tert-butyl, trifluoromethyl, 1-trifluoromethyleth-1-yl, 2-trifluoromethylprop-1-yl, 2-methylthioeth-1-yl, methoxymethyl, phenyl or benzyl;
 $R_3$ is hydrogen or methyl;
 Z is methyl, n-butyl, trifluoromethyl or pentafluoroethyl; and the symbol ⁓ represents a single or a double bond provided that a least one of the groups $R_2$ and Z contains at least one fluorine atom.

A compound of formula (II) may be obtained by a process comprising:
 (a) reacting a compound of formula (VI) wherein R, A, Y and the symbol ⁓ are as defined above with a compound of formula (VIII)

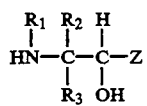  (VIII)

wherein $R_1$, $R_2$ and $R_3$ are as defined above and Z is a $C_1$-$C_6$ alkyl group unsubstituted or substituted by one or more fluorine atoms so obtaining a compound of formula (II) wherein A, R, $R_1$, $R_2$, $R_3$ and the symbol ⁓ are as defined above and Z is a $C_1$-$C_6$ alkyl group unsubstituted or substituted by one or more fluorine atoms; or (b) reacting a compound of formula (IX)

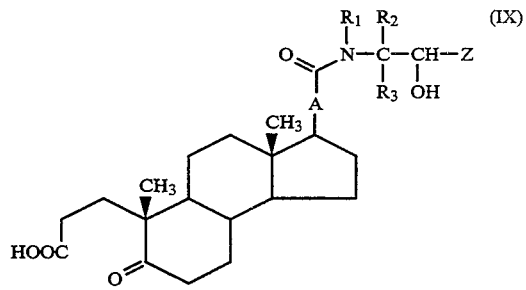

wherein $R_1$, $R_2$, $R_3$ and A are as defined above and Z is a $C_1$-$C_6$ alkyl group unsubstituted or substituted by one or more fluorine atoms with an amine of formula (X)

wherein R is as defined above so obtaining a compound of formula (XI)

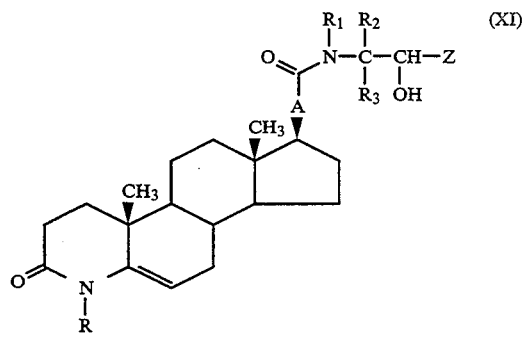

wherein A, R, $R_1$, $R_2$, and $R_3$ are as defined above and Z is a $C_1$-$C_6$ alkyl group unsubstituted or substituted by one or more fluorine atoms, and hydrogenating the compound of formula (XI) so obtaining a compound of formula (II) wherein R, $R_1$, $R_2$, $R_3$ are as defined above, Z is a $C_1$-$C_6$ alkyl group unsubstituted or substituted by one or more fluorine atoms and the symbol ⁓ is a single bond.

The reaction of a compound of formula (VI) with a compound of formula (VIII), according to the process variant (a) may be carried out, for example in a solvent such as, for example, methylene chloride, ethyl acetate, dimethylformamide or tetrahydrofurane, at a temperature ranging from about 0° C. to 100° C., optionally in the presence of an organic base such as, for example, a $C_1$-$C_6$ trialkylamine, preferably triethylamine, for a time varying from 2 hours to about 5 days.

The compounds of formula (VIII) are often used as salt-derivatives, preferably hydrochlorides, and the amino group is formed in situ in the presence of an organic base such as, for example, a $C_1$-$C_6$-trialkylamine, preferably triethylamine.

The reaction of a compound of formula (IX) with a compound of formula (X), according to the process (b) may be carried out in an anhydrous organic solvent at a temperature from about 60° C. to the reflux temperature of the solvent. It is suitably continued for a period of from about 30 minutes to about four hours.

Preferably the solvent is ethylene glycol, dimethylformamide, dimethylsulphoxide, ethanol, methanol, dioxane, ethylacetate or a mixture of any of these.

The hydrogenation of a compound of formula (XI) according to the process (b) may be carried out in an organic solvent under hydrogen pressure varying from about 1 atm to about 10 atm, in the presence of a hydrogenation catalyst. The temperature is typically from room temperature to about 100° C. The reduction time typically varies from about 30 minutes to about five hours.

Preferably the solvent is ethanol, acetic acid or a mixture of any of these and the hydrogenation catalyst is platinum oxide (Adams' Catalyst), 5% or 10% palladium on charcoal or palladium hydroxide.

A compound of formula (IX) may be obtained by the oxidation of a compound of formula (XII)

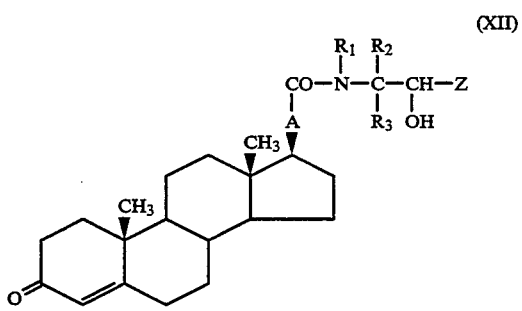

(XII)

wherein $R_1$, $R_2$, $R_3$ and A are as defined above and Z is a $C_1$-$C_6$ alkyl group unsubstituted or substituted by one or more fluorine atoms.

The oxidation of a compound of formula (XII) may be carried out, for example, in the presence of an oxidising agent such as sodium metaperiodate and potassium permanganate in an organic solvent and a base such as aqueous potassium carbonate. It is suitably performed at a temperature of from room temperature to about 60° C., typically for a period of from about one hour to about five hours.

Preferably the organic solvent is methanol, ethanol, acetone, tetrahydrofuran, dioxane, isopropanol, tert-butanol or a mixture of any of these.

The reaction is suitably performed by adding a solution of the oxidising agent, for example, sodium metaperiodate and potassium permanganate, and the base such as potassium carbonate, in water to a solution of a compound of formula (XII) in an organic solvent, or by adding simultaneously an aqueous solution of sodium metaperiodate and an aqueous solution of potassium permanganate to a solution of a compound of formula (XII) in an organic solvent and aqueous potassium carbonate.

Alternatively the oxidation of a compound of formula (XII) may be carried out with ozone in an organic solvent. The reaction is typically continued until all the starting material is consumed. The temperature of the reaction is suitably from about −78° C. to room temperature. An oxidizing agent is then added to the reaction mixture to destroy the resulting ozonide. Preferably, the solvent is methylene chloride, ethylacetate, methanol or a mixture of any of these. The oxidising agent is preferably hydrogen peroxide.

When the oxidation of a compound of formula (XII) is carried out with ozone, it is possible to perform the reaction of a compound of formula (IX) with an amine of formula (X) as above described, by treating directly the ozonide containing reaction mixture with the amine of formula (X) typically in excess, thereby directly obtaining a compound of formula (XI).

A compound of formula (III) wherein Y is an activating group of the carboxy function may be prepared reacting a compound of formula (III), wherein Y is an OH group with a suitable reagent, according to the methods used in the synthesis of amidic and peptidic linkages. For example, a compound of formula (III) wherein Y is

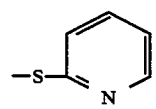

may be prepared treating a compound of formula (III), wherein Y is an OH group, with 2,2-dithio-dipyridine in the presence of triphenylphosphine in a solvent such as, for example, toluene or methylene chloride, at a temperature ranging from 0° C. to 40° C., for a time varying from half an hour to 8 hours.

A compound of formula (III) wherein Y is an OH group may be obtained hydrolysing a compound of formula (XIII)

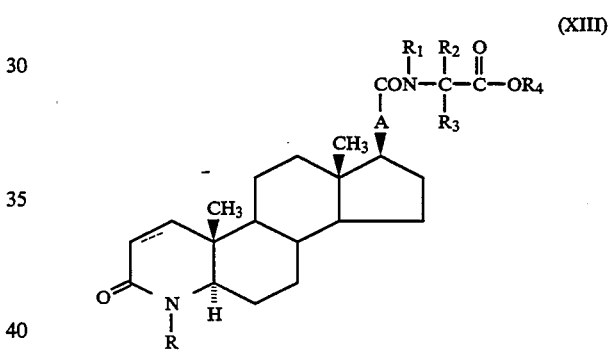

(XIII)

wherein R, $R_1$, $R_2$, $R_3$, A and the symbol ⁃⁃⁃ are as defined above and $R_6$ is a protective group of the carboxy function easily hydrolysable in suitable conditions, such as, for example, methyl, ethyl, tert-butyl, benzyl or 2,2,2-trihaloethyl.

The reaction may be carried out, for example, when $R_6$ is tert-butyl, in a solvent such as ethyl acetate, in the presence of a strong acid, e.g. gaseous hydrochloric acid, trifluoroacetic acid, at a temperature ranging from about 0° C. to about 40° C., for a time varying from about half an hour to about 24 hours.

A compound of formula (XIII) may be obtained by reacting a compound of formula (VI), wherein Y is preferably an activating group of the carboxy function with a compound of formula (XIV)

(XIV)

wherein $R_1$, $R_2$, $R_3$ and $R_8$ are as defined above.

The reaction may be carried out in a solvent such as, for example, methylene chloride, ethylacetate, benzene, dioxane, chloroform, tetrahydrofuran, dimethylformamide or acetonitrile, for a time varying from about half an hour to about 72 hours, at a temperature ranging from about 0° C. to the reflux temperature of the solvent (see, for example, Tetr. Lett. 22, 1901–904 (1970)).

The compounds of formula (VI) are known compounds (J.M.C. 29 (II) 2298–2315 (1986)).

A compound of formula (VII) may be obtained deprotecting a compound of formula (XV)

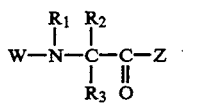

wherein $R_1$, $R_2$, $R_3$ and Z are as defined above and W is an amino protecting group commonly used in the synthesis of α-aminoacids and peptides, such as, for example, N-benzyloxycarbonyl (Cbz), N-tert-butoxycarbonyl (BOC), 2,2,2-trichloroethoxycarbonyl (TClOC), 2,2,2-tribromoethoxycarbonyl (Tbcoc), trifluoroacetyl (Tfac).

The reaction conditions for the deprotection depend on the amino protecting group used.

For example, when W is a BOC group, the reaction may be carried out in a solvent such as, for example, methylene chloride, chloroform or ethyl acetate, in the presence of a strong acid, e.g. hydrochloric acid or trifluoroacetic acid, optionally in the presence of a tert-butyl cation scavenger such as thioanisole, at a temperature from about 0° C. to about 40° C., for a time varying from half an hour to 24 hours.

A compound of formula (XV) wherein $R_1$, $R_2$, $R_3$ and W are as defined above and Z is a

group wherein $R_6$ and $R_7$ are as defined above, may be obtained reacting a compound of formula (XVI)

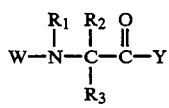

wherein $R_1$, $R_2$, $R_3$, W and Y are as defined above with a compound of formula (IV).

For example, when Y is

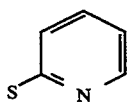

the reaction may be carried out in a solvent such as methylene chloride, ethyl acetate or dimethylformamide, for a time varying from about half an hour to 24 hours, at a temperature ranging from about 0° C. to the reflux temperature of the solvent.

The compounds of formula (XV) wherein $R_1$, $R_2$, $R_3$ and W are as defined above and Z is a $C_1$–$C_6$ alkyl group are known compounds; for example, they can be prepared starting from α-amino acids, according to the procedure reported in J.O.C. 48, 2260–2266 (1983) or to the Dakin-West reaction (J. Biol. Chem. 78, 91, 1928).

The compounds of formula (XV), wherein $R_1$, $R_2$, $R_3$ and W are as defined above and Z is a $C_1$–$C_6$ alkyl group unsubstituted or substituted by one or more fluorine atoms are known compounds or they can be obtained by known methods, for example, when Z is $CF_3$ the compounds are obtained as reported in Tetr. Lett. 27(2), 135–138 (1986) and Tetr. Lett. 27(14), 1579–1582 (1986).

The compounds of formula (IV), (V), (VIII), (X), (XII), (XIV) and (XV) wherein Z is a group $OR_5$ as defined above and the compounds of formula (XVI) are commercially available compounds or they may be prepared by known methods described in the literature.

The compounds of formulae (I) and (II) of the present invention inhibit specifically the testosterone 5α-reductase enzyme and, therefore, are potent antiandrogens.

For example, the inhibitory effect of the compounds of the invention on 5α-reductase was determined in vitro and in vivo according to the procedure reported herebelow.

In vitro assay of 5α-reductase inhibition

Inhibition of 5α-reductase was evaluated using the particulate fraction from homogenates of hyperplastic human prostates as the enzyme source. The particulate fraction was prepared centrifuging prostate homogenate at 140,000 x g. The resulting pellet, washed several times, was resuspended in buffer and stored at −80° C. in aliquots containing ≈10 mg protein/ml.

The assay for 5α-reductase was done in a final volume of 0.5 ml, in 40 mM TRIS-HCl buffer pH 5.5, containing 1 mM dithiothreitol, 5 mM NADPH, 1 μM [$^{14}$C]testosterone, an aliquot of the enzyme preparation and various concentrations of the inhibitors. After 30 min incubation at 37° C. the reaction was terminated by addition of 2 ml cold diethyl ether and the organic phase was separated, evaporated under $N_2$ and resuspended in ethyl acetate. Testosterone metabolites in this extract were separated in TLC on silica gel F 254 plates (Merck), using chloroform, acetone and n-hexane (2:1:2) as developing solvent system. Radioactivity on the plate was scanned and analysed from quantitative plots printed by a TLC-analyzer (Berthold). The fractional 5α-reduction of testosterone was calculated by relating the $^{14}$C-radioactivity in the 5α-reduced metabolites (5α-dihydrotesterone, 3α- and 3α-androstanediols) regions to the total radioactivity in the testosterone and 5α-reduced metabolites regions.

The concentration of each compound required to reduce control 5α-reductase activity by 50% ($IC_{50}$) was determined by plotting % inhibition versus log of inhibitor concentration.

In vivo inhibition of 5α-reductase

The standard test for the antiandrogenic effect in rats was used. Prepuberal 22-day-old male rats were castrated via scrotal incision under light ether anaesthesia. On the seventh day after orchiectomy, androgen replacement was performed via subcutaneous implantation of 1 cm-long Silastic ® tube (Dow-Corning, model No. 602-265) filled with a mixture of 25% testosterone and 75% cholesterol. The rats were then treated orally with the tested compounds (7 animals/group), once daily for 7 consecutive days. Twenty four hours after the last dose the rats were sacrificed and the ventral prostate was removed and weighed. Control animals (testosterone controls) received the vehicle (0.5 ml/kg of 0.5% Methocel/0.4% Tween 80). One group of castrated rats was not implanted with testosterone (castrated controls).

The mean percentage of inhibition of the T-induced hypertrophic response of the prostate was calculated according to the following formula:

$$\% \ inhibition = 100 \times (W_{TC} - W_I)/(W_{TC} - W_{CC})$$

where $W_{TC}$, $W_{CC}$ and $W_I$ are the mean prostate weight of testosterone control, castrated control and inhibitor treated group, respectively.

As an example, the results obtained with some representative compound of the invention identified by their numbers in the list previously given are shown in the following table:

TABLE 1

In vitro and in vivo inhibition of 5α-reductase

| Compound | In vitro inhibition IC$_{50}$ (nM) | % Inhibition of prostate weight at 3 mg/kg/day p.o. |
|---|---|---|
| 5 | 16 | 58 |
| 7 | 8 | 54 |
| 22 | 14 | 50 |

From the results reported in this Table it is evident that the new compounds are very potent 5α-reductase inhibitors, both in vitro and in vivo.

In view of the above indicated activity the compounds of the invention are therapeutically useful in the situations in which a decrease in androgen action, by means of 5α-reductase inhibition, is desirable such as, for example, benign prostatic hyperplasia, prostatic and breast cancers and certain skin-hair conditions such as, e.g. acne, seborrhoea, female hirsutism and male pattern baldness. A mammal, e.g. a human or animal, may thus be treated by a method which comprises administering thereto a pharmaceutically effective amount of a compound of formula (I) or (II) or a pharmaceutically acceptable salt thereof as defined above.

The toxicity of the compounds of the invention is quite negligible so that they can be safely used in therapy. The compounds of the invention can be administered in a variety of dosage forms, e.g. orally, in the form of tablets, capsules, sugar- or film-coated tablets, liquid solutions or suspensions; rectally, in the form of suppositories; parenterally, e.g. intra-muscularly, or by intravenous injection or infusion; or topically, e.g. in the form of creams.

The dosage depends on the age, weight, conditions of the patient and administration route; for example, the dosage adopted for oral administration to adult humans may range from about 1 to 200 mg pro dose, from 1 to 3 times daily.

As already said, the invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, Corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dye-stuffs; sweeteners; wetting agents, such as lecithin, polysorbates, laurylsulphates; and, in general non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be, e.g. syrups, emulsions and suspensions.

The syrups may contain as carrier, for example, saccharose or saccharose with glycerins and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycol, e.g. propylene glycol and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

Conventional carriers may be used for topical formulations.

The present invention further provides a compound of formula (I) or (II), or a pharmaceutically acceptable salt thereof, for use in a method of treatment of the human or animal body by therapy in particular for use as a testosterone α-reductase inhibitor.

The present invention further provides the use of a compound of formula (I) or (II) or a pharmaceutically acceptable salt thereof in the manufacture of a medicament for use as a testosterone 5α-reductase inhibitor.

The following Examples further illustrate the invention.

The reported NMR data are determined in CDCl$_3$.

The abbreviations THF, DMF, DDQ used in the present specification stand, respectively, for tetrahydrofuran, dimethylformamide and 2,3-dichloro-5,6-dicyanobenzoquinone. The nomenclature used to identify the compounds in the following examples, refers to a numbering of the skeleton as shown herebelow:

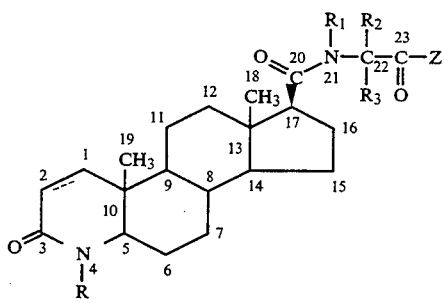

EXAMPLE 1

(22R, S)-N-(1-Neopentylcarbamoyleth-1-yl) 3-oxo-4-aza-5α-androst-1-ene-17⊕-carboxamide.

[(I),═══double bond, A=bond, R=H, R$_1$=H, R$_2$=CH$_3$, R$_3$=H, Z=NH—CH$_2$—C(CH$_3$)$_3$]

To a stirred solution of (22RS)-N-(1-neopentylcarbamoyleth-1-yl) 3-oxo-4-aza-5α-androstane-17β-carboxamide (460 mg) in anhydrous dioxane (5 ml), bis(-trimethylsilyl)trifluoroacetamide (BSTFA) (1.056 g) and 2,3-dichloro-5,6-dicyano-1,4-benzoquinone (227 mg) were added, under nitrogen atmosphere, at room temperature.

After stirring at room temperature for 4 hours, the mixture was refluxed for 20 hours.

The resulting dark solution was poured into a stirred mixture of methylene chloride (30 ml) and 1% aqueous sodium bisulphite solution (5 ml); the precipitated hydroquinone was removed by filtration, the organic layer was separated, washed with 2N HCl (5 ml), brine (5 ml) and anhydrified over sodium sulphate.

Removal of the solvent under vacuum left a dark brown oil that was purified by flash chromatography on silica gel (eluant: acetone/chloroform 1:1), so obtaining 180 mg of the title compound (m.p. 160°–175° C.).

NMR (DMSO) δ: 0.53 (s, 3H, Me(18)), 0.75 (s, 9H, tBu), 0.81 (s, 3H, Me(19)), 1.17 (d, 3H, —CONH—CH(CH$_3$)—CONH—), 2.70-3.00 (m, 2H, NH—CH$_2$—tBu), 3.16 (dd, 1H, H(5α)), 4.43 (q., 1H, —CONH—CH(CH$_3$)—CONH—), 5.72 ( bs, 1H, CONH(4)), 5.63 (dd, 1H, H(2)), 6.62 (d, 1H, H(1)), 7.35 (d, 1H, CONH(21)), 7.71 (t, 1H, CONH).

MS (m/z): 457M+· 343M−·CONH CH$_2$C(CH$_3$)$_3$]+ (100%)

EXAMPLE 2

(22RS)-N-(1-Neopentylcarbamoyleth-1-yl) 3-oxo-4-aza-5α-androstane-17β-carboxamide.

[(I),═══single bond, A=bond, R=H, R$_1$=H, R$_2$=CH$_3$, R$_3$=H, Z=NH—CH$_2$C(CH$_3$)$_3$]

To a suspension of L-Alanine tert-butyl ester hydrochloride (1.136 g) in ethylacetate (25 ml), triethylamine (0.87 ml) is added.

After stirring at room temperature for 30 minutes, 2-Pyridyl 3-oxo-4-aza-5α-androstane-17β-carbothioate (2.03 g) is added and the stirring is continued for 60 hours at room temperature.

The mixture is poured into water (250 ml) and extracted with methylene chloride (3×50 ml), the combined organic extracts are washed with lN hydrochloric acid, brine, saturated sodium hydrogen carbonate, brine and anhydrified over sodium sulphate.

The solvent is removed under vacuum and the crude solid (2.4 g) so obtained is chromatographed on silica gel (eluant ethyl acetate/methylene chloride 3:2), so obtaining 2.18 g of pure (22S)-N-(3-oxo-4-aza-5α-androstane-17β-carbonyl)alanine tert-butyl ester, which is crystallised from diethylether (1.92 g, m.p. 213°–214° C.).

920 mg of the tert-butyl ester so obtained are dissolved in methylene chloride (7 ml); trifluoroacetic acid (1.0 ml) is added and the solution is refluxed for 30 hours. The mixture is poured into a saturated aqueous solution of sodium bicarbonate (25 ml), and the organic layer is separated; the aqueous layer is washed twice with methylene chloride and acidified to pH 1-2 by slow addition of 1N hydrochloric acid; the precipitation of the free acid occurs; after aging overnight at room temperature, the precipitate is filtered and dried; recrystallization from hot chloroform affords 690 mg of N-(3-oxo-4-aza-5α-androstane-17β-carbonyl)alanine (m.p. 239°–241° C.). Mixture of epimers 22S:22R =85:15).

To a suspension of (22RS)-N-(3-oxo-4-aza-5α-androstane-17β-carbonyl) alanine (300 mg) in anhydrous toluene (3 ml), triphenylphosphine (300 mg) and dipyridyl disulfide (326 mg) were added, and the suspension was stirred for 5 hours at room temperature.

Then neopentylamine (0.629 ml) was added and the clear yellow solution was stirred at room temperature for additional 24 hours.

The solvent was removed under vacuum and the crude was chromatographed directly on silica gel eluting with acetone/chloroform 3:2, to give 240 mg of the title compound (m.p. 140°–150° C.).

NMR (DMSO) δ: 0.53 (s, 3H, Me(18)), 0.75 (s, 3H, Me(19)), 0.80 (s, 9H, tBu), 1.17 (d, 3H, —CONH—CH(CH$_3$)—CONH—), 2.70-3.00 (m, 3H, NH—CH$_2$—tBu+H(5α)), 4.43 (q, 1H, —CONH—CH(CH$_3$)—CONH—), 7.25 (bs, 1H, CONH(4), 7.35 (d, 1H, CONH(21)), 7.71 (t, 1H, CONH).

MS (m/z): 459M+· 345M−·CONH CH$_2$C(CH$_3$)$_3$]+ (100%)

EXAMPLE 3

(22RS)-N-(3-oxobut-2-yl) 3-oxo-4-aza-5α-androstane-17β-carboxamide.

[(I),═══single bond, A=bond, R=H, R$_1$=H, R$_2$=CH$_3$, R$_3$=H, Z=CH$_3$]

To a stirred suspension of (22RS)-(3-oxo-4-aza-5α-androstane-17β-carbonyl)alanine 2-pyridylthioester (725.5 mg) in anhydrous tetrahydrofurane (30 ml), cooled to −78° C., under an argon atmosphere, a solution of methylmagnesium bromide (6 ml, in tetrahydrofurane/toluene 25:75) is added dropwise.

The reaction mixture is stirred at −78° C. for 30 minutes, allowed to rise to −30° C. and then quenched with 10% ammonium chloride; the resulting solution is extracted with ethyl acetate and the organic extracts are washed with 1N sodium hydroxide, with brine and dried over sodium sulphate.

The solvent is removed under vacuum and the solid crude is chromatographed on silica gel (eluant acetone/chloroform (1:1), so obtaining 123 mg of the title compound.

NMR (CDCl$_3$) δ: 0.67 (s, 3H, Me(18)), 0.90 (s, 3H, Me(19)), 1.35 (d, 3H, CONH—CH(CH$_3$)—CO), 2.17 (s, 3H, COCH$_3$), 3.04 (dd, 1H, H(5α)), 4.62 (q., 1H, CONHCH(CH$_3$)CO), 5.34 (bs, 1H, CONH(4)), 6.20 (d, 1H, CONH(21)).

MS (m/z): 388M+·; 345M–·COCH₃]+; 274M–·CONHCH(CH₃)COCH₃]+

EXAMPLE 4

(22RS)-N-(2,2,2-Trifluoro-1-methoxycarbonylethyl) 3-oxo-4-aza-5α-androst-1-ene-17β-carboxamide.

[(I),===double bond, A=bond, R=H, R₁=H, R₂=CF₃, R₃=H, Z=OCH₃]

To a solution of 2-pyridyl 3-oxo-4-aza-5α-androst-1-ene-17β-carbothioate (410 mg) in methylene chloride (5.0 ml) 3,3,3-trifluoro-D,L-alanine methyl ester (300 mg) was added and the mixture was heated at reflux for 24 hours. The solvent was removed and the crude was chromatographed on silica gel (eluant: benzene/ethyl acetate/methanol 84:11:5) so obtaining 100 mg of a white solid compound that is crystallised from AcOEt-/Et₂O to afford 79 mg of the pure title compound (m.p. 113°–120° C.).

NMR (CDCl₃) δ: 0.67 (s, 3H, Me(18)), 0.96 (s, 3H, Me(19)), 3.32 (dd, 1H, H(5α)), 3.85 (s, 3H, COOCH₃), 5.40 (m, 2H, CONHCH(CF₃)CO+CONH(4)), 5.80 (dd, 1H, H(2)), 6.02 (d, 1H, CONH(21)), 6.77 (d, 1H, H(1)).

MS (m/z ): 456M+· 441M–·CH₃]+ 438M—H₂O]+· 425M–·OCH₃]+

Following an analogous procedure and using the appropriate starting materials, the compound listed below are prepared:

N-(3,3,3-trifluoro-2-methyl-1-methoxycarbonylprop-1-yl) 3-oxo-4-aza-5α-androst-1-ene-17β-carboxamide;

N-(4,4,4-trifluoro-3-methyl-1-methoxycarbonylbut-1-yl) 3-oxo-4-aza-5α-androst-1-ene-17β-carboxamide.

EXAMPLE 5

(22S)-N-(3-oxo-hept-2-yl) 3-oxo-4-aza-5α-androst-1-ene-17β-carboxamide.

[(I),===double bond, A=bond, R=H, R₁=H, R₂=CH₃, R₃=H, Z=nBu]

To a stirred solution of N-BOC-(L)-alanine (3.784 g, 20 mmol) in freshly distilled tetrahydrofurane (60 ml), a solution of n-butyl lithium (12.5 ml; 1.6M in n-hexane) was added, dropwise, at −10° C., under a nitrogen atmosphere.

The clear solution was cooled at −78° C. and a further amount of n-butyl lithium (25 ml, 1.6M in n-hexane) was added dropwise.

After stirring at −78° C. for ½ h the reaction mixture was allowed to reach room temperature and, after 1 h at room temperature the reaction was poured into a diluted solution of ammonium chloride and ice (400 ml) and extracted with ether (3×100 ml).

The organic extracts were washed with saturated ammonium chloride solution, with brine, with water and anhydrified over sodium sulphate.

Evaporation of the solvent under vacuum affords a crude oil that is purified by flash chromatography on silica gel (eluant ethyl acetate/n-hexane 20:80), so obtaining 1.45 g of (2S)-N-BOC-2-aminoheptan-3-one.

(2S)-N-BOC-2-aminoheptan-3-one (1.45 g) was dissolved in ethyl acetate (25 ml); the solution was cooled at about −50° C. and saturated with gaseous hydrochloric acid.

After stirring at room temperature overnight, the solvent was removed under vacuum and the yellow oil so obtained was treated with diethyl ether (5 ml), thus affording 662 mg of (2S)-2-aminoheptan-3-one hydrochloride as a white solid. To a stirred solution of 2-pyridyl 3-oxo-4-aza-5α-androst-1-ene-17β-carbothioate (340 mg) in anhydrous methylene chloride (20 ml) and triethylamine (0.694 ml), a solution of (S)-2-aminoheptan-3-one hydrochloride (410 mg) in anhydrous methylene chloride (25 ml) is added dropwise during 1 hour.

The mixture is stirred at room temperature for 18 hours and then the solvent is removed under vacuum and the yellow crude is chromatographed on silica gel (eluant: chloroform/ethyl acetate 50:50), so affording 210 mg of the title compound (m.p. 218°–220° C. from ethyl acetate).

Elemental analysis Calculated for $C_{26}H_{40}N_2O_3$: C 72.86 H 9.41 N 6.53 found: C 72.42 H 9.05 N 6.46

NMR (CDCl₃) δ: 0.68 (s, 3H, Me(18)), 0.90 (t, 3H, (CH₂)₃CH₃), 0.96 (s, 3H, Me(19)), 1.35 (d, 3H, —CONH—CH(CH₃)CO—), 2.50 ( 2dt, 2H, COCH₂CH₂—), 3.26 (dd, 1H, H(5α)), 4.62 (q, 1H, —CONHCH(CH₃-)CO—), 5.34 (bs, 1H, CONH(4)), 5.81 (dd, 1H, H(2)), 6.20 (d, 1H, CONH(21)), 6.77 (d, 1H, H(1)).

IR (nujol): 3410, 3190, 1712, 1665, 1600 cm⁻¹

MS (m/z): 428M+· 343M–·CO(CH₂)₃CH₃]+ 272M–·CONHCH(CH₃)CO(CH₂)₃CH₃]+ (100%)

EXAMPLE 6

(22S)-N-(3-methylthio-1-methoxycarbonylprop-1-yl) 3-oxo-4-aza-5α-androst-1-ene-17β-carboxamide

[(I),===double bond, A=bond, R=H, R₁=H, R₂=CH₂CH₂SCH₃, R₃=H, Z=OCH₃]

To L-methionine methyl ester hydrochloride (206.3 mg) in methylene chloride (5 ml), triethylamine (0.138 ml) is added; after 10 minutes 2-pyridyl 3-oxo-4-aza-5α-androst-1-ene-17β-carbothioate (826 mg) is added to the cloudy solution.

After stirring at room temperature for 24 hours, the mixture is loaded directly on a silica gel column and eluted with methylene chloride/ethyl acetate 50:50, so obtaining 300 mg of solid yellow compound, which is crystallised from boiling ethyl acetate/methylene chloride (3:1). After filtering and drying under vacuum, 230 mg of the title compound are obtained (m.p. 228°–229° C.).

Elemental analysis Calculated for $C_{25}H_{38}N_2O_4S$: C 64.90 H 8.28 N 6.05 S 6.93 found: C 64.48 H 8.15 N 5.95 S 7.09

NMR (CDCl₃) δ: 0.68 (s, 3H, Me(18)), 0.96 (s, 3H, Me(19)), 2.00 (m, 2H, —CH—CH₂CH₂SCH₃), 2.10 (s, 3H, SCH₃), 2.55 (t, 2H, —CH₂SCH₃), 3.32 (dd, 1H, H(5α)), 3.75 (s, 3H, COOCH₃), 4.85 (m, 1H, CONHCHCO), 5.25 (bs, 1H, CONH(4)), 5.81 (dd, 1H, H(2)), 6.03 (d, 1H, CONH(21)), 6.78 (d, 1H, H(1)).

MS (m/z): 462M+· 401M—CH₂SCH₃]+ 388M—CH₂=CHSCH₃]+

Following an analogous procedure and using the appropriate starting materials, the compounds listed below are prepared:

N-(2-methoxy-1-methoxycarbonyleth-1-yl) 3-oxo-4-aza-5α-androst-1-ene-17β-carboxamide.

EXAMPLE 7

(22RS)-N-(5-methyl-2-oxohex-3-yl) 3-oxo-4-aza-5α-androst-1-ene-17β-carboxamide.

-[(I),===double bond, A=bond, R=H, R$_1$=H, R$_2$=—CH$_2$CH(CH$_3$)$_2$, R$_3$=H, Z=CH$_3$]

A suspension of D,L leucine (1.0 g) in pyridine (3.34 ml) and acetic anhydride (3.34 ml) is refluxed for 6.0 hours and then at room temperature overnight.

After diluting with water and 1N hydrochloric acid, the mixture is extracted thoroughly with methylene chloride. The organic layers are washed with 1N hydrochloric acid, with water until neutral and anhydrified over sodium sulphate.

After evaporating the solvent, the crude brownish oil is purified by flash chromatography on silica gel (eluant: methylene chloride/acetone 90:10), so obtaining 624 mg of (3RS)-N-acetyl-3-amino-5-methylhexan-2-one as a clear oil. To (3RS)-N-acetyl-3-amino-5-methylhexan-2-one (564 mg) dissolved in acetic acid (2.2 ml), concentrated hydrochloric acid (4 ml) is added and the mixture is refluxed for 6 hours. The solvents are evaporated under vacuum, the crude is treated with a little anhydrous ethanol and the product is precipitated by slow addition of diethylether.

After filtering, washing with diethyl ether and drying under vacuum, 383 mg of (3R, S)-3-amino-5-methylhexan-2-one hydrochloride are obtained.

A mixture of 2-pyridyl 3-oxo-4-aza-5α-androst-1-ene-17β-carbothioate (450 mg) in methylene chloride (22 ml) and (3R, S)-3-amino-5-methylhexan-2-one hydrochloride (271 mg) is treated with triethylamine (0.458 ml).

The yellow solution is stirred at room temperature for 5 days.

After removing the solvent under vacuum the crude is purified by flash chromatography (eluant: methylene chloride/acetone 75:25), so obtaining 530 mg of the title compound.

Elemental analysis Calculated for C$_{26}$H$_{40}$N$_2$O$_3$: C 72.86 H 9.41 N 6.53 found: C 71.40 H 9.50 N 6.28

NMR (CDCl$_3$) δ: 0.65 (s, 3H, Me (18)), 0.94 (s+d, 9H, Me (19)+CH(CH$_3$)$_2$), 2.11 (s, 3H, COCH$_3$), 3.31 (dd, 1H, H(5α)), 4.70 (m, 1H, CONH—CH—COCH$_3$), 5.48 (s, 1H, CONH(4)), 5.80 (dd, 1H, H(2)), 5.87 (d, 1H, CONH(21)), 6.77 (d, 1H, H(1)).

MS (m/z): 428M+·413M-·CH$_3$]+ 385M-·CH(CH$_3$)]+ 300 385-·C$_4$H$_7$NO]+ 272 300—CO]+ 86 ·C$_5$H$_{12}$N]+ (100%)

Following an analogous procedure and using the appropriate starting materials, the compounds listed below are prepared:

(22RS)-N-(3-oxobut-2-yl) 3-oxo-4-aza-5α-androst-1-ene-17β-carboxamide.

NMR (CDCl$_3$) δ: 0.65 and 0.68 (2s, 3H. Me(18)), 0.97 (s, 3H, Me(19)), 1.38 (d, 3H, —NHCH(CH$_3$)COCH$_3$), 2.24 (s, 3H, COCH$_3$), 3.33 (dd, 1H, H(5α)), 4.63 (m, 1H, NHCH(CH$_3$)COCH$_3$), 5.40 (s, 1H, NH(4)), 5.80 (dd, 1H, H(2)), 6.10 and 6.20 (2d, 1H, NH(21)), 6.78 (d, 1H, H(1)).

MS (m/z): 386M+·371M-·CH$_3$]+ 343M-·COCH$_3$]+

(22RS)-N-(4-methyl-2-oxopent-3-yl) 3-oxo-4-aza-5α-androst-1-ene-17β-carboxamide

NMR (CDCl$_3$) δ: 0.75 and 0.81 (2s, 3H, Me(18)), 0.96 (s, 3H, Me(19)), 0.79 and 1.02 (2d, 6H, isopropylic methyls), 2.03 (s, 3H, COCH$_3$), 3.33 (dd, 1H, H(5α)), 4.72 (m, 1H, H(22)), 5.25 (s, 1H, NH(4)), 5.81 (dd, 1H, H(2)), 5.85 and 5.92 (2d, 1H, NH(21)), 6.78 (d, 1H, H(1)).

MS (m/z): 414M+·

N-(4-methyl-2-oxohex-3-yl) 3-oxo-4-aza-5α-androst-1-ene-17β-carboxamide;

N-(5,5,5-trifluoro-4-methyl-2-oxopent-3-yl) 3-oxo-4-aza-5α-androst-1-ene-17β-carboxamide;

N-(6,6,6-trifluoro-5-methyl-2-oxohex-3-yl) 3-oxo-4-aza-5α-androst-1-ene-17β-carboxamide;

N-(5-methylthio-2-oxopent-3-yl) 3-oxo-4-aza-5α-androst-1-ene-17β-carboxamide;

N-(4-methoxy-2-oxobut-3-yl) 3-oxo-4-aza-5α-androst-1-ene-17β-carboxamide.

EXAMPLE 8

(22RS)-N-(1,1,1-trifluoro-3-oxobut-2-yl) 3-oxo-4-aza-5α-androst-1-ene-17β-carboxamide.

[(I):===double bond, A=single bond, R=H, R$_1$=H, R$_2$=CF$_3$, R$_3$=H, Z=CH$_3$]

D,L-Trifluoroalanine (159 mg) in dry pyridine (0.6 ml) is treated with acetic anhydride (0.6 ml) and stirred at room temperature for 4.5 hours. The reaction mixture is then acidified with 1N hydrochloric acid and extracted several times with methylene chloride; the combined organic layers are washed with water, dried over sodium sulphate and evaporated. The crude so obtained is purified by flash chromatography (eluant: methylene chloride/ethyl acetate 80:20) to afford 117 mg of (2RS)-N-acetyl 1,1,1-trifluoro-2-aminobutan-3-one.

A solution of the α-acetylaminoketone (50 mg) in 1 ml of a mixture of concentrated hydrochloric acid/ethanol/water (2:1:1) is refluxed for 6 hours. The reaction mixture is evaporated to dryness under vacuum, the residue is dissolved in the minimum amount of absolute ethanol and diethyl ether is added dropwise until further addition causes no more precipitation. The precipitate is collected by filtration, washed with ether and dried, so obtaining 20 mg of (2RS)-1,1,1-trifluoro-2-aminobutan-3-one hydrochloride. A stirred solution of 2-pyridyl 3-oxo-4-aza-5α-androst-1-ene-17β-carbothioate (237 mg) and (2RS)-1,1,1-trifluoro-2-amino-butan-3-one hydrochloride (153 mg) in methylene chloride (10 ml) is treated dropwise with triethylamine (0.241 ml). After 4 hours the reaction mixture is evaporated to dryness and the crude is purified by flash chromatography (eluant: methylene chloride/acetone 60:40), so affording 93 mg of the title compound.

NMR (CDCl$_3$) δ: 0.67 (s, 3H, Me(18)), 0.96 (s, 3H, Me(19)), 2.11 (s, 3H, —COCH$_3$), 3.32 (dd, 1H, H(5α)), 5.25 (m, 1H, CONH—CH(CF$_3$)—CO—), 5.40 (s, 1H, CONH(4)), 5.80 (dd, 1H, H(2)), 6.02 (d, 1H, CONH(21)), 6.77 (d, 1H, H(1)).

EXAMPLE 9

(22RS)-N-(1,1,1-trifluoro-2-oxobut-3-yl) 3-oxo-4-aza-5α-androst-1-ene-17β-carboxamide.

[(I):===double bond, A=single bond, R=H, R$_1$=H, R$_2$=CH$_3$, R$_3$=H, Z=CF$_3$]

D,L-Alanine is N-benzoylated by standard procedures and the benzamido derivative (1.59 g) is cyclized to the corresponding oxazol-5-one by brief (~15 minutes) warming to 80° C. with acetic anhydride (2.9 ml). The reaction mixture is then concentrated under vacuum in a rotatory evaporator and vacuum distilled twice with toluene.

The residue is treated with trifluoroacetic anhydride (3.1 ml) and heated under reflux for 1.75 hours and then at room temperature overnight. The volatiles are then removed thoroughly under vacuum and the residue is treated with oxalic acid (1.2 g) and stirred at 110° C. for 20 minutes. The reaction mixture is then diluted with water, and extracted with ethyl acetate (5×30 ml); the organic layers are anhydrified over sodium sulphate and the solvent evaporated under vacuum.

The crude so obtained is purified by flash chromatography on silica gel (eluant: ethyl acetate/n-hexane 30:70) to afford a solid material that is crystallized from carbon tetrachloride; there are obtained 410 mg of (3RS)-N-benzoyl 1,1,1-trifluoro-3-aminobutan-2-one, partially in the hydrate form.

A solution of the ketone-hydrate mixture (404 mg) in ethanol (3 ml), cooled to 0° C., is treated with sodiumborohydride (NaBH$_4$, 62 mg). The reaction mixture is stirred at room temperature for 4 hours, then it is acidified with 6N hydrochloric acid and extracted with ethyl acetate; the organic extracts are washed with water, dried over sodium sulphate and flush-evaporated to afford 404 mg of (2RS-3RS)-N-benzoyl 1,1,1-trifluoro-3-aminobutan-2-ol.

A solution of trifluorobenzamidoalcohol (333 mg) in 94 ml of a mixture of concentrated hydrochloric acid/ethanol/water (2:1:1) was stirred under reflux for 23 hours. The reaction mixture was then evaporated under vacuum and the residue dissolved in water (13 ml) and extracted several times with diethyl ether. Flush evaporation of the aqueous layer afforded a pale-green solid that, after trituration with ethyl acetate, gave 190 mg of (2RS-3RS)-1,1,1-trifluoro-3-amino-butan-2-ol hydrochloride as a white solid (mixture of both pairs of enantiomers).

A stirred solution of 2-pyridyl 3-oxo-4-aza-5α-androst-1-ene-17β-carbothioate (344 mg) and (2RS-3RS)-1,1,1-trifluoro-3-amino-butan-2-ol hydrochloride in methylene chloride (14 ml) is treated dropwise with triethylamine (0.175 ml). After 2 days the reaction mixture was evaporated to dryness and purified by flash chromatography on silica gel (eluant: methylene chloride/acetone 70:30) to afford 338 mg of (22RS-23RS)-N-(1,1,1-trifluoro-2-hydroxybut-3-yl) 3-oxo-4-aza-5α-androst1-ene-17β-carboxamide [(II),====double bond, A=single bond, R=H, R$_1$=H, R$_2$=CH$_3$, R$_3$=H, Z=CF$_3$]

MS (m/z): 442M+·(100%) 427M−·CH$_3$]+

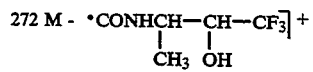

IR (CHCl$_3$): 1700, 1670 cm$^{-1}$

NMR (CDCl$_3$) δ: 0.70 (s, 3H, He(18)), 0.97 (s, 3H, He(19)), 1.3 (d, 3H, CONHCHCH$_3$CH(OH)—), 3.33 (dd, 1H, H(5α)), 4.05 (m, 1H, —CH(OH)CF$_3$), 4.31 (m, 1H, CONHCH(CH$_3$)), 4.90 and 5.05 (2m, 1H, OH), 5.39 (s, 1H, NH(4)), 5.54 (m, 1H, NH(21)), 5.8 (dd, 1H, H(2)), 6.78 (d, 1H, H(1)).

A solution of (22RS-23RS)-N-(1,1,1-trifluoro-2-hydroxybut-3-yl) 3-oxo-4-aza-5α-androst-1-ene-17β-carboxamide (110 mg) in methylene chloride (1,1 ml) is added within 20 minutes to a stirred solution of oxalyl chloride (0.095 ml) and dimethylsulfoxide (0.171 ml) in methylene chloride (2.0 ml), prepared according to the usual procedure, at −10° C. The reaction temperature is maintained for 15 minutes, triethylamine (0.173 ml) is added dropwise and then the mixture is allowed to warm to room temperature. Water is added and the aqueous layer is extracted several times with ethyl acetate.

The combined organic extracts are washed with water, dried over sodium sulphate and the solvent is removed under vacuum.

Purification of the crude by flash chromatography (methylene chloride/acetone 70:30) affords 73 mg of the title compound, as a mixture of trifluoroketone and its hydrate form.

MS (m/z): 458M+· hydrated form 440M+· ketone form 425M−·CH$_3$]+ 343M−·COCF$_3$]+ 300M−·NH—CH(CH$_3$)COCF$_3$]+

IR (CDCl$_3$): 3260, 3170, 1770, 1700, 1670 cm$^{-1}$

NMR (CDCl$_3$) δ: 0.70 (s, 3H, Me(18)), 0.97 (s, 3H, Me(19)), 1.35 and 1.45 (2d, 3H, NHCH(CH$_3$)COCF$_3$ hydrate and ketone forms), 3.33 (dd, 1H, H(5α)), 4.15 and 5.00 (2m, 1H, NHCH(CH$_3$) COCF$_3$ hydrate and ketone forms), 5.70–6.05 (m, NH(4)+NH(21) hydrate and ketone forms+OH hydrate form), 5.80 (dd, 1H, H(2)), 6.78 (d, 1H, H(1)).

Following an analogous procedure and using the D,L-valine as starting material, (22RS-23RS)-N-(1,1,1-trifluoro-4-methyl-2-hydroxypent-3-yl) 3-oxo-4-aza-5α-androst-1-ene-17β-carboxamide [(II): ====double bond, A=single bond, R=H, R$_1$=H, R$_2$=CH(CH$_3$)$_2$, R$_3$=H, Z=CF$_3$] is prepared:

MS (m/z): 470M+·455M−·CH$_3$]+

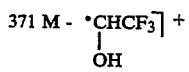

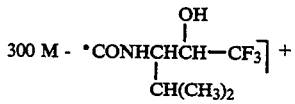

NMR (CDCl$_3$) δ: 0.78 (s, 3H, Me(18)), 1.00 (s, 3H, Me(19)), 1.00–1.15 (2d, 6H, CH(CH$_3$)$_2$), 3.33 (dd, 1H, H(5α)), 3.85–4.40 (2m, 2H, NHCH(iPr)CH(OH)CF$_3$), 5.10 (bm, 1H, OH), 5.45 (d, 1H, NH(21)), 5.55 (bs, 1H, NH(4)), 5.80 (dd, 1H, H(2)), 6.80 (d, 1H, H(1)).

The oxidation of this compound by the Swern reagent affords (22RS)-N-(1,1,1-trifluoro-4-methyl-2-oxopent-3-yl) 3-oxo-4-aza-5α-androst-1-ene-17β-carboxamide [(I):====double bond, A=single bond, R=H, R$_1$=H, R$_2$=CH(CH$_3$)$_2$, R$_3$=H, Z=CF$_3$] as a mixture or epimers almost exclusively in the ketone form.

MS (m/z): 486M+· hydrated form 468M+· ketone form 453M−·CH$_3$]+ 371M−·COCF$_3$]+

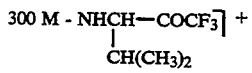

NMR (CDCl$_3$) δ: 0.64 and 0.70 (2s, 1H, Me(18)), 0.97 (s, 3H, Me(19)), 0.85 and 1.05 (4d, 6H, CH(CH$_3$)$_2$), 3.33 (dd, 1H, H(5α)), 5.05 (2m, 1H, NH—CH(iPr)COCF$_3$), 5.55 (s, 1H, NH(4)), 5.63 and 5.75 (2d, 1H, NH(21)), 5.80 (dd, 1H, H(2)), 6.77 (d, 1H, H(1)).

Following an analogous procedure and using phenylalanine as starting material, N-(1,1,1-trifluoro-2-oxo-4-phenylbut-3-yl) 3-oxo-4-aza-5α-androst-1-ene-17β-carboxamide was obtained.

Following an analogous procedure and using pentafluoropropionic anhydride instead of trifluoroacetic anhydride, the corresponding pentafluoroketones are obtained, e.g., starting from alanine, N-(1,1,1,2,2-pentafluoro-3-oxopent-4-yl) 3-oxo-4-aza-5α-androst-1-ene17β-carboxamide was obtained.

EXAMPLE 10

N-(1,1,1-trifluoro-3-methyl-2-oxobut-3-yl) 3-oxo-4-aza-5α-androst-1-ene-17β-carboxamide.

[(I):===double bond, A=single bond, R=H, R₁=H, R₂=CH₃, R₃=CH₃, Z=CF₃]

A mixture of triflouroacetaldehyde ethyl hemiacetal (2.58 ml), 2-nitropropane (1.81 ml) and potassium carbonate (111 mg) is stirred at 65° C. (oil bath temperature) for 6 hours followed by 2.5 days at room temperature. The reaction mixture is diluted with water (100 ml) and extracted with methylene chloride (100 ml+5×50 ml). The combined organic layers are dried over sodium sulphate and the solvent is evaporated under reduced pressure. Purification of the liquid residue by flash chromatography on silica gel (eluant n-hexane/ethylacetate 85:15) affords 3-methyl-3-nitro-1,1,1-trifluorobutan-2-ol as an oil (2.005 g)

NMR (CDCl₃)δ: 1.75 (m, 6H, 2CH₃), 3.1 (m, 1H, OH), 4.75 (m, 1H, CF₃CH—)

The β-nitroalcohol (2.005 g) in 95% ethanol (50 ml) is reduced in a Parr shaker under 50 psi of hydrogen pressure, with Raney Nickel (W-2) as catalyst. The catalyst is filtered off, the solution is treated with 37% hydrochloric acid and the solvent is evaporated under vacuum, so affording a solid residue which is further purified by recrystallisation from ethanol/diethyl ether: 1,663 g of (2RS)-3-amino-3-methyl-1,1,1-trifluorobutan-2-ol hydrochloride are obtained (m.p. 237°–245° dec).

A stirred solution of 2-pyridyl 3-oxo-4-aza-5α-androst-1-ene-17β-carbothioate (500 mg) and (2R, S)-3-amino-3-methyl-1,1,1-trifluoro-butan-2-ol hydrochloride (470 mg) in anhydrous dimethylformamide (20 ml) is treated dropwise with triethylamine (0.509 ml) and then is heated to 100° C. for 18 hours.

After diluting with benzene to a volume of about 150 ml, the reaction mixture is washed with water (150 ml) with 1N hydrochloric acid (2×25 ml), with water until neutral and dried over sodium sulphate. The solvent is evaporated under vacuum and the crude residue is purified by flash chromatography on silica gel (eluant: Benzene/ethylacetate/methanol 82:10:8) to yield 466 mg of (23RS)-N-(1,1,1-trifluoro-2-hydroxy-3-methylbut-3-yl) 3-oxo-4-aza-5α-androst-1-ene-17β-carboxamide [(II): ===double bond, A=single bond, R=H, R₁=H, R₂=CH₃, R₃=CH₃, Z=CF₃]

MS (m/z): 456M⁺·441M-·CH₃]⁺

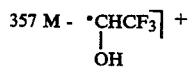

NMR (CDCl₃) δ: 0.70 (s, 3H, Me(18)), 0.97 (s, 3H, Me(19)), 1.40 and 1.50 (2s, 6H, NH—C(CH₃)₂—CH-(OH)CF₃), 3.33 (m, 1H, H(5α)), 3.70 (m, 1H, OH), 3.90 (m, 1H, —CH(OH)CF₃), 5.45 (s, 1H, NH(4)), 5.70 (s, 1H, NH(21)), 5.82 (dd, 1H, H(2)), 6.77 (d, 1H, H(1)).

A solution of (23RS)-N-(1,1,1-trifluoro-2-hydroxy-3-methylbut-3-yl) 3-oxo-4-aza-5α-androst-1-ene-17β-carboxamide (250 mg) in methylene chloride (3 ml) is added, within 20 minutes, to a stirred solution of oxalyl chloride (0.211 ml) and dimethylsulfoxide (0.373 ml) in methylene chloride (7 ml) (prepared according to the Swern procedure at about −60° C.), maintaining the temperature at −21° C., under an inert atmosphere of nitrogen. After 15 minutes triethylamine (0.381 ml) is added dropwise and then the reaction mixture is allowed to warm to room temperature.

After staying at room temperature overnight the mixture is diluted with methylene chloride (70 ml) and water (30 ml); the organic layer is separated, is dried over sodium sulphate and the solvent is-evaporated under reduced pressure.

The crude foam so obtained is purified by flash chromatography on silica gel (eluant: methylene chloride/acetone 80:20) to yield the title compound, as a foam which solidifies by treatment with diethylether (m.p. 283°–286° C.), almost completely in the ketone form.

MS (m/z): 472M⁺·hydrate form 454M⁺·ketone form 439M-·CH₃]⁺ 357M-·COCF₃]⁺ 300M-·NH—C(CH₃)-2COCF₃]⁺

NMR (CDCl₃) δ: 0.68 (s, 3H, Me(18)), 0.97 (s, 3H, Me(19)), 1.52 (s, 6H, NH—C(CH₃)₂—COCF₃), 3.33 (dd, 1H, H(5α)), 5.45 (s, 1H, NH(4)), 5.75 (s, 1H, NH(21)), 5.82 (dd, 1H, H(2)), 6.77 (d, 1H, H(1)).

Following an analogous procedure and using the appropriate starting material the below reported compounds were obtained:

N-(3-methyl-2-oxobut-3-yl) 3-oxo-4-aza-5α-androst-1-ene-17β-carboxamide [(I):===double bond, A=single bond, R =H, R₁=H, R₂=CH₃, R₃=CH₃, Z=CH₃];

N-(1,1,1-trifluoro-2-oxo-3-phenylpropyl) 3-oxo-4-aza-5α-androst-1-ene-17β-carboxamide;

N-(1,1,1-trifluoro-3-methyl-2-oxo-3-phenylpropyl) 3-oxo-4-aza-5α-androst-1-ene-17β-carboxamide.

EXAMPLE 11

(22RS)-N-(4,4-dimethyl-2-oxopent-3-yl) 3-oxo-4-aza-5α-androst-1-ene-17β-carboxamide [(I):====double bond, A=single bond, bond, R=H, R₁=H, R₂=CH(CH₃)₃, R₃=H, Z=CH₃]

To a stirred solution of (L)-tert-butyl-leucine (3.1 g) in 1N sodium hydroxide (23.6 ml), maintained at about 15° C., ethyl chloroformate (2.3 ml) is added portionwise over about 1 hour while maintaining the pH between 9.0 and 9.5 by eventual addition of 1N sodium hydroxide.

After stirring for half an hour at pH 9.5, the solution is cooled to 0° C., washed twice with diethylether, acidified with 40% phosphoric acid to pH 1.0 and extracted with methylene chloride. The organic extracts are dried over sodium sulphate and the solvent is removed under vacuum.

The crude is purified by chromatography on silica gel (eluant n-hexane/ethylacetate/acetic acid 70:30:1) so affording 4.5 g of N-(ethoxycarbonyl)-L-tert-butyl-leucine.

To N-(ethoxycarbonyl)-L-tert-butyl-leucine (980 mg) dissolved in freshly distilled tetrahydrofurane (25 ml) methyllithium (2.78 ml of a 1.57M solution in diethyl ether) is added while cooling at −10° C. under inert atmosphere of nitrogen.

After stirring at −10° C. for 15 minutes, the reaction mixture is cooled to about −40° C. and further methyl lithium (8.37 ml of a 1.57M solution in diethylether) is added.

After stirring at −35° C. for 1 hour the reaction mixture is allowed to warm to room temperature and stirred for 14 hours, and then it is poured into ice-cooled 40% H₃PO₄ (100 ml) and extracted with ethyl acetate (4×50 ml). The organic extracts are washed with NaHCO₃, with brine, dried over sodium sulphate and the solvent is evaporated under vacuum. The crude is purified by chromatography on silica gel (eluant n-hexane/ethylacetate 80:20) thus affording 140 mg of N-ethoxycarbonyl-3-amino-4,4-dimethyl-pentan-2-one.

N-ethoxycarbonyl-3-amino-4,4-dimethyl-pentan-2-one (203 mg) is dissolved in 48% aqueous hydrobromic acid (4 ml) and the solution is stirred under reflux for 6 hours. The reaction mixture is then evaporated under reduced pressure to give a solid residue, that is further purified by recrystallisation (from ethanol/diethylether) to afford 149 mg of pure (3RS)-3-amino-4,4-dimethyl-pentan-2-one hydrobromide (m.p. 218°–220° C.)

NMR (CDCl₃) δ: 1.1 (s, 9H, tBu), 2.35 (s, 3H, COCH₃), 4.15 (s, 1H, —CH(tBu))

A solution of 2-pyridyl 3-oxo-4-aza-5α-androst-1-ene-17β-carboxylate (100 mg) and (3RS)-3-amino-4,4-dimethylpentan-2-one hydrobromide (64 mg) in methylene chloride (4 ml) is treated dropwise with triethylamine (0.051 ml) and the mixture is stirred at room temperature for 3.5 days. The solvent is evaporated under reduced pressure and the residue is purified by flash chromatography on silica gel (eluant methylene chloride/acetone 80:20) to yield 81 mg of the title compound (1:1 mixture of both epimers)

MS (m/z): 428M⁺

NMR (CDCl₃) δ: 0.62 and 0.72 (2s, 3H, Me(18)), 0.97 (s, 3H, Me(19)), 1.00 (s, 9H, tBu), 2.28 (s, 3H, COCH₃), 3.33 (dd, 1H, H(5α)), 4.55 (m, 1H, CH(tBu)), 5.38 (s, 1H, NH(4)), 5.81 (dd, 1H, H(2)), 5.90 (m, 1H, NH(21)), 6.78 (d, 1H, H(1)).

EXAMPLE 12

(22RS)-N-(1,1,1-trifluoro-2-oxobut-3-yl) 3-oxo-4-aza-5α-androstane-17β-carboxamide [(I): ===double bond, A=single bond, R=H, R₁=H, R₂=CH₃, R₃=H, Z=CF₃]

To a stirred solution of (2RS-3RS)-1,1,1-trifluoro-3-amino-butan-2-ol hydrochloride (525 mg) (obtained as described in the example 9) in methylene chloride (30 ml), triethylamine (0.39 ml) is added, at room temperature. After 30 minutes solid 2-pyridyl 3-oxo-androst-4-ene-17β-carbothioate (1.00 g) is added and the mixture is refluxed for 24 hours. After diluting with methylene chloride the reaction mixture is washed with 1N hydrochloric acid, water until neutrality and dried over sodium sulphate. The solvent is removed under vacuum and the crude (1.1 g) is purified by flash chromatography (eluant: n-hexane/ethylacetate 60:40) so obtaining 890 mg of solid (22RS-23RS)-N-(1,1,1-trifluoro-2-hydroxybut-3-yl) 3-oxo-androst-4-ene-17β-carboxamide [(XII): A=single bond, R₁=H, R₂=CH₃, R₃=H, Z=CF₃]

To a solution of (22RS-23RS)-N-(1,1,1-trifluoro-2-hydroxybut-3-yl) 3-oxo-androst-4-ene-17β-carboxamide (690 mg) in tert-butanol (9 ml) and 2M aqueous sodium carbonate (1.04 ml), a 2% aqueous potassium permanganate solution (0.882 ml) and a 0.75M sodium metaperiodate aqueous solution (17.5 ml) are added dropwise simultaneously, at such a rate that the colour of the reaction mixture remains always pink (over about 30 minutes) at about 35°–40° C.

After stirring at 40° C. for 3 hours, the reaction mixture is cooled to 30° C., filtered and the tert-butanol is removed under vacuum. By slow addition of 1N hydrochloric acid, at about 0° C., the precipitation of the crude keto-acid occurs. Purification of the crude by flash chromatography (eluant ethyl acetate/n-hexane 70/30) affords 260 mg of (22RS-23RS)-17β-[N-(1,1,1-trifluoro-2-hydroxybut-3-yl)carbamoyl]-5-oxo-4-nor-3,5-secoandrostan-3-oic acid [(IX): A=single bond, R₁=H, R₂=CH₃, R₃=H, Z =CF₃]

A suspension of the secoacid so obtained (260 mg) in ethylene glycol (3.0 ml) is saturated at 0° C. with gaseous ammonia: the secoacid dissolves completely. The solution so obtained is heated slowly at 180° C. over about 1 hour and maintained at this temperature for 20 minutes.

After cooling to room temperature and diluting with water, the reaction mixture is extracted with methylene chloride. The combined organic extracts are washed with water until neutrality, dried over sodium sulphate and the solvent is evaporated under vacuum.

Purification of the brown crude so obtained, by flash chromatography on silica gel (eluant: methylene chloride/acetone 80:20) affords 150 mg of (22RS-23RS)-N-(1,1,1-trifluoro-2-hydroxybut-3-yl) 3-oxo-4-aza-androst-5-ene-17β-carboxamide. [(XI): A=single bond, R=H, R₁=H, R₂=CH₃, R₃=H, Z=CF₃].

A solution of (22RS-23RS)-N-(1,1,1-trifluoro-2-hydroxybut-3-yl) 3-oxo-4-aza-androst-5-ene-17β-carboxamide (150 mg) in glacial acetic acid is hydrogenated in the presence of PtO₂ (Adams' catalyst) under a pressure of 45 psi of hydrogen at 45° C.

The reaction mixture is cooled, the catalyst is filtered off and the solvent is removed under reduced pressure. The residue is taken up with methylene chloride, washed with 1N sulphuric acid, with brine, with sodium carbonate, with brine, with water, dried over sodium sulphate and the solvent is removed under vacuum. The crude is purified by flash chromatography on silica gel (eluant methylene chloride/acetone 70:30) to afford 132 mg of (22RS-23RS)-N-(1,1,1-trifluoro-2-hydroxybut-3-yl) 3-oxo-4-aza-5α-androstane-17β-carboxamide. [(II):===single bond, A=single bond, R=H, R₁=H, R₂=CH₃, R₃=H, Z=CF₃].

The oxidation of the trifluoroalcohol so obtained with the Swern reaction, analogously to the example 9, affords (22RS-23RS)-N-(1,1,1-trifluoro-2-oxo-but-3-yl) 3-oxo-4-aza-5α-androstane-17β-carboxamide. [(I): ===single bond, A=single bond, R=H, R₁=H, R₂=CH₃, R₃=H, Z=CH₃].

EXAMPLE 13

Scored tablets for oral use, each containing 250 mg of the active substance, were manufactured as follows.

| Composition (for 10,000 tablets) | |
|---|---|
| N-[1,1,1-trifluoro-2-oxobut-3-yl] 3-oxo-4-aza-5α-androst-1-ana-17β-carboxamide | 2500 g |
| corn starch | 275 g |
| talc powder | 187 g |
| calcium stearate | 38 g |

The active substance was granulated with a 4% w/v aqueous solution of methyl cellulose. To the dried granules a mixture of the remainder of the ingredients is added and the final mixture compressed into tablets of proper weight.

EXAMPLE 14

Two-piece hard gelatin capsules for oral use, each containing 250 mg of active substance were manufactured as follows.

| Compositions for 10,000 capsules | |
|---|---|
| N-[1,1,1-trifluoro-2-oxobut-3-yl] 3-oxo-4-aza-5α-androst-1-ene-17β-carboxamide | 2500 g |
| lactose | 1000 g |
| corn starch | 300 g |
| talc powder | 65 g |
| calcium stearate | 35 g |

The active substance was mixed with the starch-lactose mixture followed by the talc and calcium stearate.

EXAMPLE 15

Scored tablets for oral use, each containing 250 mg of the active substance, were manufactured as follows.

| Composition (for 10,000 tablets) | |
|---|---|
| N-[1,1,1-trifluoro-2-oxobut-3-yl] 3-oxo-4-aza-5α-androst-1-ene-17β-carboxamide | 2500 g |
| corn starch | 280 g |
| talc powder | 180 g |
| calcium stearate | 40 g |

The active substance was granulated with a 4% w/v aqueous solution of methyl cellulose. To the dried granules a mixture of the remainder of the ingredients is added and the final mixture compressed into tablets of proper weight.

We claim:

1. A compound of the following formula (I):

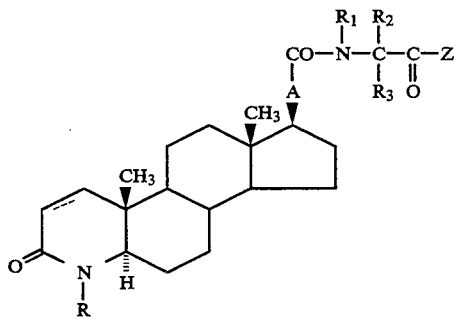

wherein:

R is a hydrogen atom or a $C_1$–$C_4$ alkyl group unsubstituted or substituted by one or more fluorine atoms;

A is a single bond or a straight or branched $C_1$–$C_6$ alkylene chain;

$R_1$ is a hydrogen atom or a $C_1$–$C_6$ alkyl group unsubstituted or substituted by one or more fluorine atoms;

$R_2$ is:
(a) a $C_1$–$C_6$ group unsubstituted or substituted by one or more substituents chosen from fluoro, $C_1$–$C_4$ alkoxycarbonyl, carbamoyl, carboxy, hydroxy, $C_1$–$C_4$ alkoxy, amino, di-$C_1$–$C_4$ alkylamino, mercapto and $C_1$–$C_4$ alkylthio, or
(b) a $C_5$–$C_7$ cycloalkyl or a $C_6$–$C_{10}$ cycloalkylalkyl group, unsubstituted or substituted by one or more fluorine atoms, or (c) a phenyl or a benzyl group, unsubstituted or ring substituted by one or more substituents chosen from halogen, $C_1$–$C_4$ alkyl, $C_1$–$C_4$ alkoxy, hydroxy and trifluoromethyl, or (d) (4-imidazolyl)methyl, (3-imidazolyl)methyl and (3-indolyl)methyl, unsubstituted or ring substituted by one or more fluorine atoms;

$R_3$ is hydrogen, a $C_1$–$C_4$ alkyl group, or a phenyl or a benzyl group, unsubstituted or ring substituted by one or more substituents chosen from halogen, $C_1$–$C_4$ alkyl, $C_1$–$C_4$ alkoxy, hydroxy and trifluoromethyl;

Z is:
(a') a $C_1$–$C_6$ alkyl group unsubstituted or substituted by one or more fluorine atoms,
(b') an —$OR_5$ group wherein $R_5$ is a $C_1$–$C_6$ alkyl group,
(c') a

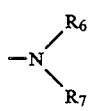

group wherein each of $R_6$ and $R_7$, independently, is hydrogen, $C_1$–$C_6$ alkyl, $C_5$–$C_7$ cycloalkyl or phenyl or $R_6$ and $R_7$ taken together with the nitrogen to which they are linked form a piperidyl, piperazinyl or morpholino ring; and the symbol ⁓ represents a single or a double bond; provided that when Z is a group $OR_5$
$R_2$ is
a) a $C_1$–$C_6$ alkyl group substituted by one or more substituents chosen from fluoro, $C_1$–$C_4$ alkoxycarbonyl, carbamoyl, carboxy, C–$C_4$-alkoxy, amino, di-$C_1$–$C_4$ alkylamino, mercapto and $C_1$–$C_4$ alkylthio, or
b) a $C_5$–$C_7$ cycloalkyl or a $C_6$–$C_{10}$ cycloalkylalkyl group, unsubstituted or substituted by one or more fluorine atoms and pharmaceutically acceptable salts thereof.

2. A compound according to claim 1 wherein:

R is hydrogen or methyl;

A is a single bond;

$R_1$ is hydrogen;

$R_2$ is methyl, iso-propyl, iso-butyl, sec-butyl, tert-butyl, trifluoromethyl, 1-trifluoromethyleth-1-yl, 2-trifluoromethylprop-1-yl, 2-methylthioeth-1-yl, methoxymethyl, phenyl or benzyl;

$R_3$ is hydrogen or methyl;

Z is methyl, n-butyl, trifluoromethyl, pentafluoroethyl, a group $OR_5$ wherein $R_5$ is methyl, ethyl or tert-butyl, or a group

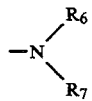

wherein each of $R_6$ and $R_7$ is, independently, hydrogen, ethyl, isopropyl or neopentyl; and the symbol ⁓ represents a single or a double bond provided that when Z is a group $OR_5$, $R_2$ is trifluoromethyl, 1-trifluoromethyleth-1-yl, 2-trifluoromethylprop-1-yl, 2-methylthioethyl, methoxymethyl.

3. A compound selected from the group consisting of
N-(1-neopentylcarbamoyleth-1-yl) 3-oxo-4-aza-5α-androstane-17β-carboxamide;

N-(1-neopentylcarbamoyleth-1-yl) 3-oxo-4-aza-5α-androst-1-ene-17β-carboxamide;
N-[3-oxobut-2-yl]3-oxo-4-aza-5α-androstane-17β-carboxamide;
N-[3-oxohept-2-yl]3-oxo-4-aza-5α-androst-1-ene-17β-carboxamide;
N-[1,1,1-trifluoro-2-oxobut-3-yl]3-oxo-4-aza-5α-androst-1-ene-17β-carboxamide;
N-[4-methyl-2-oxopent-3-yl]3-oxo-4-aza-5α-androst-1-ene-17β-carboxamide;
N-[1,1,1-trifluoro-4-methyl-2-oxopent-3-yl]3-oxo-4-aza-5α-androst-1-ene-17β-carboxamide;
N-[5-methyl-2-oxohex-3-yl]3-oxo-4-aza-5α-androst-1-ene-17β-carboxamide;
N-[4-methyl-2-oxohex-3-yl]3-oxo-4-aza-5α-androst-1-ene-17β-carboxamide;
N-[4,4-dimethyl-2-oxopent-3-yl]3-oxo-4-aza-5α-androst-1-ene-17β-carboxamide;
N-[1,1,1-trifluoro-3-oxobut-2-yl]3-oxo-4-aza-5α-androst-1-ene-17β-carboxamide;
N-[2,2,2-trifluoro-1-methoxycarbonyleth-1-yl]3-oxo-4-aza-5α-androst-1-ene-17β-carboxamide;
N-[5,5,5-trifluoro-4-methyl-2-oxopent-3-yl]3-oxo-4-aza-5α-androst-1-ene-17β-carboxamide;
N-[3,3,3-trifluoro-2-methyl-1-methoxycarbonylprop-1-yl]3oxo-4-aza-5α-androst-1-ene-17β-carboxamide;
N-[6,6,6-trifluoro-5-methyl-2-oxohex-3-yl]3-oxo-4-aza-5α-androst-1-ene-17β-carboxamide;
N-[4,4,4-trifluoro-3-methyl-1-methoxycarbonylbut-1-yl]3-oxo-4-aza-5α-androst-1-ene-17β-carboxamide;
N-[5-methylthio-2-oxopent-3-yl]3-oxo-4-aza-5α-androst-1-ene-17β-carboxamide;
N-[3-methylthio-1-methoxycarbonylprop-1-yl]3-oxo-4-aza-5α-androst-1-ene-17β-carboxamide;
N-[4-methoxy-2-oxobut-3-yl]3-oxo-4-aza-5α-androst-1-ene-17β-carboxamide;
N-[2-methoxy-1-methoxycarbonyleth-1-yl]3-oxo-4-aza-5α-androst-1-ene-17β-carboxamide;
N-[3-oxobut-2-yl]3-oxo-4-aza-5α-androst-1-ene-17β-carboxamide;
N-[1,1,1-trifluoro-3-methyl-2-oxobut-3-yl]3-oxo-4-aza-5α-androst-1-ene-17β-carboxamide;
N-[3-methyl-2-oxobut-3-yl]3-oxo-4-aza-5α-androst-1-ene-17β-carboxamide;
N-[1,1,1-trifluoro-2-oxo-4-phenylbut-3-yl]3-oxo-4-aza-5α-androst-1-ene-17β-carboxamide;
N-[1,1,1-trifluoro-2-oxo-3-phenylpropyl]3-oxo-4-aza-5α-androst-1-ene-17β-carboxamide;
N-[1,1,1-trifluoro-3-methyl-2-oxo-3-phenylpropyl]3-oxo-4-aza-5α-androst-1-ene-17β-carboxamide; and
N-[1,1,1,2,2-pentafluoro-3-oxopent-4-yl]3-oxo-4-aza-5α-androst-1-ene-17β-carboxamide;
and the pharmaceutically acceptable salts thereof.

4. A pharmaceutical composition for inhibiting testosterone 5α-reductase comprising a pharmaceutically acceptable carrier or diluent and, as an active principle, an effective amount to achieve said inhibition of a compound of formula (I) according to claim 1 or a pharmaceutically acceptable salt thereof.

* * * * *

UNITED STATES PATENT AND TRADEMARK OFFICE
CERTIFICATE OF CORRECTION

PATENT NO. : 5,418,238
DATED : MAY 23, 1995
INVENTOR(S) : PANZERI, ET AL.

It is certified that error appears in the above-indentified patent and that said Letters Patent is hereby corrected as shown below:

In the Abstract, line 22, "testosterone 68 5α-reductase" should read --testosterone 5α-reductace--.

Column 28, line 38, "CH(CH$_3$)$_3$" should read --C(CH$_3$)$_3$--.

Column 31, line 61, "C$_1$-C$_6$ group" should read --C$_1$-C$_6$ alkyl group--.

Column 32, line 31, "symbol    represents" should read --symbol .... represents--;

line 36, "C-C$_4$-alkoxy" should read --C$_1$-C$_4$-alkoxy--;

line 41, "atoms" should read --atoms;--

Signed and Sealed this

First Day of October, 1996

Attest:

BRUCE LEHMAN

*Attesting Officer*     *Commissioner of Patents and Trademarks*